(12) United States Patent
Liu et al.

(10) Patent No.: US 12,310,963 B2
(45) Date of Patent: May 27, 2025

(54) PYRAZOLE DERIVATIVES AND USE THEREOF

(71) Applicant: Tarapeutics Science Inc., Anhui (CN)

(72) Inventors: Qing Song Liu, Anhui (CN); Jing Liu, Anhui (CN); Xi Xiang Li, Anhui (CN); Ao Li Wang, Anhui (CN); Feng Ming Zou, Anhui (CN); Cheng Chen, Anhui (CN); Qing Wang Liu, Anhui (CN); Juan Liu, Anhui (CN); Jiang Yan Cao, Anhui (CN); Wen Liang Wang, Anhui (CN); Shuang Qi, Anhui (CN); Wen Chao Wang, Anhui (CN); Bei Lei Wang, Anhui (CN); Li Wang, Anhui (CN)

(73) Assignee: Tarapeutics Science Inc., Anhui (CN)

( * ) Notice: Subject to any disclaimer, the term of this patent is extended or adjusted under 35 U.S.C. 154(b) by 660 days.

(21) Appl. No.: 17/637,860

(22) PCT Filed: Aug. 14, 2020

(86) PCT No.: PCT/CN2020/109130
§ 371 (c)(1),
(2) Date: Feb. 24, 2022

(87) PCT Pub. No.: WO2021/036814
PCT Pub. Date: Mar. 4, 2021

(65) Prior Publication Data
US 2022/0288064 A1    Sep. 15, 2022

(30) Foreign Application Priority Data
Aug. 29, 2019    (CN) .......................... 201910807395.9

(51) Int. Cl.
| A61K 31/496 | (2006.01) |
| A61K 31/444 | (2006.01) |
| A61K 31/5377 | (2006.01) |
| A61P 35/00 | (2006.01) |

(52) U.S. Cl.
CPC .......... *A61K 31/496* (2013.01); *A61K 31/444* (2013.01); *A61K 31/5377* (2013.01); *A61P 35/00* (2018.01)

(58) Field of Classification Search
CPC ................ A61K 31/496; A61K 31/444; A61K 31/5377; A61P 35/00
See application file for complete search history.

(56) References Cited

U.S. PATENT DOCUMENTS 7,531,560 B2    5/2009    Cogan et al.

FOREIGN PATENT DOCUMENTS

| CN | 101501023 A | 8/2009 |
| EA | 200900072 A1 | 6/2009 |
| EA | 026152 B1 | 3/2017 |
| JP | 2009-542771 A | 12/2009 |
| JP | 2013-523614 A | 6/2013 |
| WO | 2011/117381 A1 | 9/2011 |

OTHER PUBLICATIONS

Hu L, Zheng Y, Li Z, Wang Y, Lv Y, Qin X, Zeng C. Design, synthesis, and biological activity of phenyl-pyrazole derivatives as BCR-ABL kinase inhibitors. Bioorg Med Chem. Jul. 1, 2015;23(13):3147-52. doi: 10.1016/j.bmc.2015.04.083. Epub May 12, 2015. PMID: 26022079. (Year: 2015).*
Betsholtz C. et al., "Developmental Roles of Platelet-Derived Growth Factors", BioEssays 23:494-507 (2001).
Cools J. et al., "A Tyrosine Kinase Created by Fusion of the PDGFRA and FIP1L1 Genes as a Therapeutic Target of Imatinib in Idiopathic Hypereosinophilic Syndrome", The New England Journal of Medicine 348(13):1201-1214 (Mar. 27, 2003).
Daihong L. et al., "Research Progress on Platelet-Derived Growth Factor Receptor Inhibitors", Anti-Tumor Pharmacy 3(1):2-6 and 21 (Feb. 2013), together with an English-language abstract.
Sandy J.R. et al., "Signal Transduction", British Journal of Orthodontics 25(4):269-274 (Nov. 1998).
Schaller J.L. et al., "Rapid and Complete Control of Idiopathic Hypereosinophilia With Imatinib Mesylate", MedGenMed 3(5):9 (2001).
Schermuly R.T. et al., "Reveral of Experimental Pulmonary Hypertension by PDGF Inhibition", The Journal of Clinical Investigation 115(10):2811-2821 (Oct. 2005).

(Continued)

*Primary Examiner* — Matthew P Coughlin
*Assistant Examiner* — Anna Gracw Kuckla
(74) *Attorney, Agent, or Firm* — Scully, Scott, Murphy & Presser, P.C.

(57) ABSTRACT

Provided is a novel PDGFR kinase inhibitor, comprising a compound of formula (I) or a pharmaceutically acceptable salt, solvate, ester, acid, metabolite or prodrug thereof. Further provided are use and a method of the compound of formula (I) for preventing or treating conditions associated with PDGFR kinase activity, particularly use and a method for preventing or treating conditions associated with PDGFRα and/or PDGFRβ kinase activity.

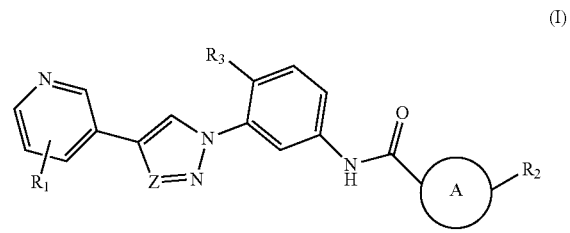

(I)

15 Claims, 3 Drawing Sheets

(56) References Cited

OTHER PUBLICATIONS

International Search Report dated Oct. 14, 2020 received International Application No. PCT/CN2020/109130, together with an English-language translation.

Russian Office Action dated Jan. 30, 2023 received in Russian Application No. 2022102500/04(005390), together with an English-language translation.

Japanese Notice of Reasons for Refusal dated Apr. 11, 2023 received in Japanese Patent Application No. 2022-513158, together with an English-language translation.

* cited by examiner

PYRAZOLE DERIVATIVES AND USE THEREOF

TECHNICAL FIELD

The present application relates to a compound as a selective PDGFR kinase inhibitor, and a method and use for inhibiting the activity of a PDGFR kinase and for treating a disease associated with inhibition of PDGFR kinase activity with such a compound.

BACKGROUND OF THE INVENTION

Platelet derived growth factor (PDGF) is a family of effective mitogens for almost all the mesenchyme-derived cells. There are four PDGF isoforms of A, B, C, and D, which form five different disulfide-linked dimer proteins of PDGF-AA, -BB, -AB, -CC and -DD. These growth factors exert their cellular effects through two structurally related tyrosine kinase receptors of PDGF receptor α (PDGFRα) and PDGF receptor β (PDGFRβ) (Sandy, J. R. (1998) *Br. J. Orthod.* 25:269-74; Betsholtz, C., et al., (2001) *BioEssays* 23:494-507).

PDGFRα is similar to PDGFRβ in its structure, and can form heterodimers and homodimers. PDGF-BB and PDGF-DD are primary activators of ββ homodimers. PDGF-AA only activates aa receptor dimers, while PDGF-AB, PDGF-BB and PDGF-CC activate both aa and αβ receptor dimers. The dimer ligand molecule binds to two receptor proteins simultaneously, and induces dimerization of receptors, autophosphorylation of specific residues in a receptor cytoplasmic domain, and cell signaling.

Structural remodeling of pulmonary vasculature is the pathomorphological basis of chronic hypoxic pulmonary hypertension, which is mainly manifested by the proliferation and migration of smooth muscle cells of the tunica media. The proliferation of smooth muscle cells depends on the effects of various growth factors, especially platelet derived growth factor. The growth factors function to regulate the proliferation of cells by binding to growth factor receptors and activating tyrosine protein kinase (TPK) in the receptors for phosphorylation. Schermuly et al. reported on JCI in 2005 that imatinib as a PDGFR inhibitor can significantly improve the symptoms of pulmonary hypertension (Schermuly, R. T., et al. 2005. Reversal of experimental pulmonary hypertension by PDGF inhibition. *J. Clin. Invest.* 115:2811-2821. doi:10.1172/JCI24838.). The authors also examined the lung tissue of patients with pulmonary hypertension undergoing lung transplantation and observed a significantly increased level of PDGF expression in patients with pulmonary hypertension. The authors believe that PDGFR inhibitors may be a new therapy for pulmonary hypertension clinically.

In addition, chronic eosinophilic leukemia (CEL) is a type of hypereosinophilic syndrome (HES). Chronic eosinophilic leukemia is a rare and unexplained disease of blood system having a continuously increased level of eosinophilic granulocyte complicated with multiple organ damage. In 2001, Schaller et al. reported for the first time imatinib mesylate (trade name: Gleevec, a small molecule inhibitor of ABL, KIT and PDGFR tyrosine kinases) in the treatment of 1 case of HES patient with a significant efficacy, and thereby proposed that HES may have inherent activations of ABL, KIT, PDGFR or other unknown target genes (Schaller, J. L., & Burkland, G. A. (2001). Case report: rapid and complete control of idiopathic hypereosinophilia with imatinib mesylate. *MedGenMed.*, 3 (5), 9). In 2003, Cools et al. detected the FIP1L1-PDGFRα fusion gene in HES patients and EOL-1 cells cultured in vitro (chronic eosinophilic leukemia cell line), which not only identified the molecular target of Gleevec for the treatment of HES to provide powerful molecular markers for the diagnosis and treatment of HES, but also revealed at the molecular level that HES is a malignant clonal disease of the hematopoietic system in essence (Cools J., DeAngelo D. J., Gotlib J., A tyrosine kinase created by fusion of the PDGFRA and FIP1L1 genes as a therapeutic target of imatinib in idiopathic hypereosinophilic syndrome. *N. Engl. J. Med.* 2003, 348 (13): 1201-14). Studies of Cools et al. demonstrated that activator of transcription 5 (STAT5) is a downstream target of the FIP1L1-PDGFRα fusion gene effect, and the activation of STAT5 contributes to the proliferation of eosinophilic granulocyte.

Examples of currently reported selective inhibitors for both PDGFRα and PDGFRβ include CP-673451 (CAS No.: 343787-29-1; molecular weight: 417.5) and imatinib (CAS No.: 152459-95-5; molecular weight: 493.60), each of which, however, is not good enough in its selectivity. In addition to the inhibitory effect for PDGFRα and β, they also inhibit the inhibitory effect for cKIT, BCR-ABL, and the like. Therefore, it is necessary to provide a selective PDGFR inhibitor in order to provide a research basis for a precise targeted therapy.

The present inventors have found a selective PDGFR inhibitor through experiments, which can significantly inhibit the tumor growth in a mouse EOL-1 cell tumor transplantation model, and can also improve the survival of rats and alleviate the conditions of pulmonary hypertension in a rat pulmonary hypertension model.

SUMMARY OF THE INVENTION

The present invention provides a selective PDGFR kinase inhibitor, comprising a compound of formula (I) or a pharmaceutically acceptable salt, solvate, ester, acid, metabolite or prodrug thereof:

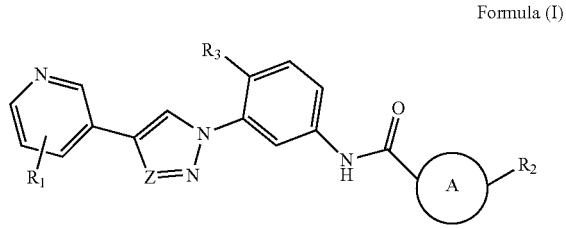

Formula (I)

wherein,
the A ring is a pyridine ring;
Z is selected from the group consisting of N and CH;
$R_1$ is selected from the group consisting of heterocycloalkyl, heterocycloalkyloxy, heterocycloalkyl $C_{1-6}$ alkoxy, heterocycloalkylamino, heterospirocycloalkyl, heterospirocycloalkylamino, $C_{3-6}$ cycloalkyl $C_{1-6}$ alkoxy, $C_{3-6}$ cycloalkyloxy, wherein the heterocycloalkyl is a 4- to 8-membered heterocycloalkyl containing oxygen and/or nitrogen atom(s), and the nitrogen atom in the heterocycloalkyl is optionally substituted with $C_{1-6}$ alkyl;
$R_2$ is selected from the group consisting of halogen and $C_{1-6}$ haloalkyl;
$R_3$ is selected from the group consisting of $C_{1-6}$ alkyl and halogen.

Preferably, the "heterocycloalkyl" as described above is a 4- to 6-membered heterocycloalkyl containing oxygen and/or nitrogen atom(s), such as, pyrrolidinyl, morpholinyl, piperazinyl, tetrahydropyranyl, tetrahydrofuranyl, oxetanyl, azetidinyl, and the like, and the nitrogen atom in those heterocycloalkyl groups is optionally substituted with $C_{1-6}$ alkyl. In another respect, the "heterospirocycloalkyl" as described above may be selected from 6- to 10-membered spirocycloalkyl groups containing oxygen and/or nitrogen heteroatom(s).

In a preferred embodiment, the A ring is selected from the group consisting of

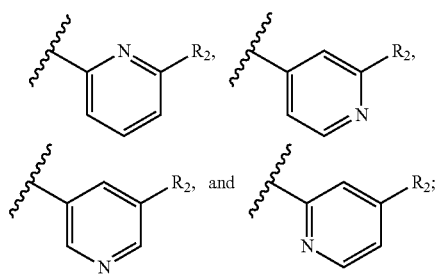

$R_2$ is selected from the group consisting of fluorine, chlorine and trifluoromethyl.

In another preferred embodiment, $R_3$ is selected from the group consisting of methyl, fluorine and chlorine.

In one respect, the present invention provides a selective PDGFR kinase inhibitor, comprising a compound of formula (Ia) or a pharmaceutically acceptable salt, solvate, ester, acid, metabolite or prodrug thereof:

Formula (Ia)

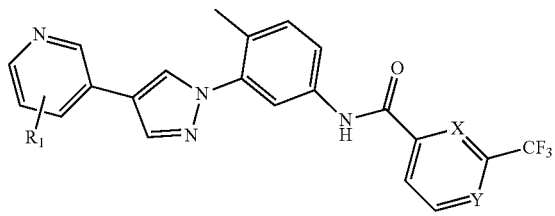

wherein, $R_1$ is selected from the group consisting of heterocycloalkyl, heterocycloalkyloxy, heterocycloalkyl $C_{1-6}$ alkoxy, heterocycloalkylamino, heterospirocycloalkyl, heterospirocycloalkylamino, $C_{3-6}$ cycloalkyl $C_{1-6}$ alkoxy, $C_{3-6}$ cycloalkyloxy, wherein the heterocycloalkyl is a 4- to 6-membered heterocycloalkyl containing oxygen and/or nitrogen atom(s), and the nitrogen atom in the heterocycloalkyl is optionally substituted with $C_{1-6}$ alkyl; and one of Y and Z is CH and the other is N.

In this embodiment, the "heterocycloalkyl" and "heterospirocycloalkyl" are as described above.

In a preferred embodiment of the present invention, R; is selected from the group consisting of $C_{1-6}$ alkyl piperazinyl (such as, N-methyl piperazinyl, e.g., 4-methyl-piperazin-1-yl), morpholinyl (such as, N-morpholinyl), tetrahydropyranyl $C_{1-6}$ alkoxy (such as, tetrahydropyran-4-yl methoxy), oxetanyloxy (such as, oxetan-3-yloxy), morpholino $C_{1-6}$ alkoxy (such as, 2-morpholinoethoxy), tetrahydrofuranyl $C_{1-6}$ alkoxy (such as, tetrahydrofuran-2-yl methoxy), $C_{3-6}$ cycloalkyl $C_{1-6}$ alkoxy (such as, cyclopentyl methoxy) and oxa-aza-spiroheptyl (such as, 2-oxa-6-aza-spiro[3.3]hept-6-yl).

The substituent of $R_1$ is preferably substituted on the carbon at a para- or meta-position of the N atom in the pyridine ring, and more preferably, is substituted on the carbon at a meta-position of the N atom in the pyridine ring.

In another respect, the present invention also provides a pharmaceutical composition, comprising a compound as described above or a pharmaceutically acceptable salt, solvate, ester, acid, metabolite or prodrug thereof, and a pharmaceutically acceptable carrier or excipient, and optionally other therapeutic agent.

In still another respect, the present invention also provides a method or use of such a compound or pharmaceutical composition for inhibiting the activity of a tyrosine kinase (wild type or various mutants or a combination thereof) and for treating, preventing or ameliorating a disease, disorder or condition which is modulated or affected by, or involved in the activity of a tyrosine kinase (wild type or various mutants or a combination thereof), wherein the tyrosine kinase may be PDGFR.

The present invention also relates to a tyrosine kinase inhibitor which selectively exhibits stronger inhibitory effect on PDGFR relative to one or more of the targets of cKIT, BCR-ABL, FLT3 and VEGFR2, and use and a method of the tyrosine kinase inhibitor of the present invention for selectively inhibiting PDGFR.

DETAILED DESCRIPTION OF THE INVENTION

Terminology

Figure 1A:
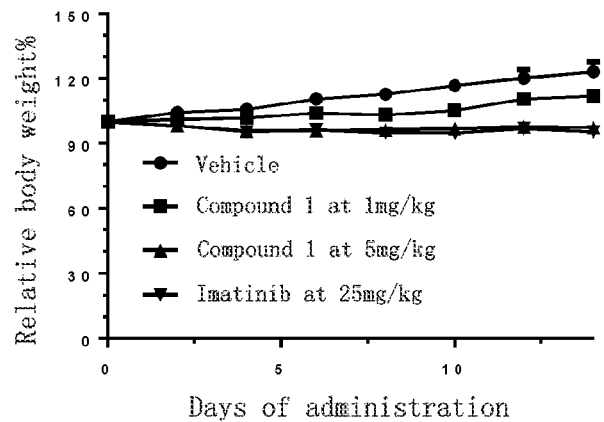
FIG. 1a shows the change in the mean body weight of mice over time in different treatment groups using Compound 1, imatinib and vehicle in a mouse tumor model of human chronic eosinophilic leukemia cells EOL-1.

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the present disclosure. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed by conventional methods well known in the art and as described in various general and more specific references that are cited and discussed throughout the present specification.

The term "alkyl" refers to an aliphatic hydrocarbon group, which may be a branched or straight alkyl group. Depending on the structure, an alkyl group may be a monoradical or a diradical (i.e., an alkylene group). In the present invention, the alkyl group is preferably an alkyl having 1 to 8 carbon atoms, more preferably a "lower alkyl" having 1 to 6 carbon atoms, and still more preferably an alkyl having 1 to 4 carbon atoms. Typical alkyl groups include, but are not limited to, methyl, ethyl, propyl, butyl, pentyl, hexyl, and the like. It should be understood that the "alkyl" as referred to herein includes all possible configurations and conformations of the alkyl which may be present. For example, the "propyl" as referred to herein includes n-propyl and iso-propyl. The "butyl" as referred to herein includes n-butyl, iso-butyl and tert-butyl. The "pentyl" as referred to herein includes n-pentyl, iso-pentyl, neo-pentyl, tert-pentyl, pent-3-yl, and the like.

The term "alkoxy" refers to an-O-alkyl group, where alkyl is as defined herein. Typical alkoxy groups include, but are not limited to, methoxy, ethoxy, propoxy, butoxy, pentyloxy, hexyloxy, and the like.

The term "cycloalkyl" refers to a monocyclic or polycyclic radical that contains only carbon and hydrogen. Cycloalkyl groups include groups having 3 to 10 ring atoms. Depending on the structure, a cycloalkyl group can be a monoradical or a diradical (e.g., a cycloalkylene group). In the present invention, a cycloalkyl group is preferably a cycloalkyl having 3 to 8 carbon atoms, and more preferably a "lower cycloalkyl" having 3 to 6 carbon atoms. Examples of cycloalkyls include, but are not limited to, cyclopropyl, cyclobutyl, cyclopentyl, cyclohexyl, cycloheptyl, cyclooctyl, cyclopentenyl, cyclohexenyl, cycloheptenyl and diamantanyl.

As used herein, the term "heterocycloalkyl" or "heterocyclyl" refers to a non-aromatic ring wherein one or more atoms forming the ring is a heteroatom selected from the group consisting of nitrogen, oxygen and sulfur. The heterocycloalkyl ring may be a monocyclic or polycyclic ring formed from three, four, five, six, seven, eight, nine, or more than nine atoms. The heterocycloalkyl ring may be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, oxetane, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group may be a monoradical or a diradical (i.e., a heterocycloalkylene group).

As used herein, the term "spirocycloalkyl" refers to a 6- to 10-membered polycyclic aliphatic hydrocarbyl group wherein two separate rings share one carbon atom. The term "heterospirocycloalkyl" refers to a spirocycloalkyl wherein one or more atoms forming the ring is a heteroatom selected from the group consisting of nitrogen, oxygen and sulfur.

The term "optional" means that one or more events described later may or may not occur, and include both events that occur and events that do not occur. The term "optionally substituted" or "substituted" means that the referenced group may be substituted with one or more additional group(s) which are each independently selected from the group consisting of alkyl, cycloalkyl, aryl, heteroaryl, heterocyclyl, hydroxy, alkoxy, cyano, halo, amide, nitro, haloalkyl, amino, methyl sulfonyl, alkyl carbonyl, alkoxy carbonyl, heteroaryl alkyl, heterocycloalkyl alkyl, aminoacyl, amino protective group, and the like. Among others, the amino protective group is preferably selected from the group consisting of pivaloyl, tert-butyloxycarbonyl, benzyloxycarbonyl, 9-fluorenylmethoxycarbonyl, benzyl, p-methoxybenzyl, allyloxycarbonyl, trifluoroacetyl, and the like.

As used herein, the term "tyrosine protein kinase" (TPK) refers to a class of kinases that catalyze the transfer of the y-phosphate from ATP to tyrosine residue on proteins and that are capable of catalyzing the phosphorylation of tyrosine residue of various protein substrates, and thus have an important effect in cell growth, proliferation and differentiation.

As used herein, the terms "inhibit", "inhibitory", or "inhibitor" used in connection with a kinase refer to inhibition of phosphotransferase activity.

A "metabolite" of a compound as disclosed herein is a derivative of that compound that is formed when the compound is metabolized. The term "active metabolite" refers to a biologically active derivative of a compound that is formed when the compound is metabolized. The term "metabolism" as used herein refers to the sum of the processes (including, but not limited to, hydrolysis reactions and reactions catalyzed by enzymes, such as, oxidation reactions) by which a particular substance is changed by an organism. Thus, enzymes may cause specific structural alterations to give a compound. For example, cytochrome P450 catalyzes a variety of redox reactions while diphosphate glucuronyl transferases catalyze the transfer of an activated glucuronic acid molecule to aromatic alcohol, aliphatic alcohol, carboxylic acid, amine and free mercapto group. Further information on metabolism may be obtained from *The Pharmacological Basis of Therapeutics,* 9th Edition, McGraw-Hill (1996). Metabolites of the compound as disclosed herein can be identified either by administration of the compound to a host and analysis of tissue samples from the host, or by incubation of hepatic cells with the compound in vitro and analysis of the resulting compound. Both methods are well known in the art. In some embodiments, metabolites of a compound are formed by oxidation processes and correspond to the respective hydroxy-containing compound. In some embodiments, a compound is metabolized to pharmacologically active metabolites. The term "modulate" as used herein means to interact with a target either directly or indirectly so as to alter the activity of the target, including, by way of example only, to enhance the activity of the target, to inhibit the activity of the target, to limit the activity of the target, or to prolong the activity of the target.

As used herein, the term "target protein" refers to a protein molecule or a portion of a protein capable of being bound by a selective binding compound. In certain embodiments, the target protein is tyrosine kinase PDGFR (including its wild-type or various mutants or a combination thereof).

As used herein, $GI_{50}$ refers to a drug concentration required for 50% growth inhibition of cells, i.e., a drug concentration at which the growth of 50% cells (such as, cancer cells) can be inhibited or controlled by the drug.

As used herein, $IC_{50}$ refers to an amount, concentration or dosage of a particular test compound that achieves a 50% inhibition of a maximal response, in an assay that measures such response.

The Novel Kinase Inhibitor of the Present Invention

The present invention provides a selective PDGFR kinase inhibitor, comprising a compound of formula (I) or a pharmaceutically acceptable salt, solvate, ester, acid, metabolite or prodrug thereof:

Formula (I)

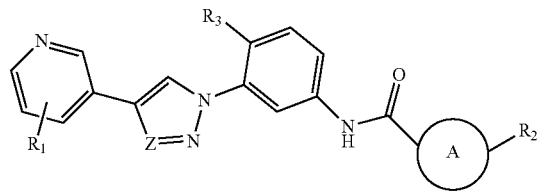

wherein, the A ring is a pyridine ring;

Z is selected from the group consisting of N and CH;

$R_1$ is selected from the group consisting of heterocycloalkyl, heterocycloalkyloxy, heterocycloalkyl $C_{1-6}$ heterocycloalkylamino, heterospirocycloalkyl, heterospirocycloalkylamino, $C_{3-6}$ cycloalkyl $C_{1-6}$ alkoxy, $C_{3-6}$ cycloalkyloxy, wherein the heterocycloalkyl is a 4- to 8-membered heterocycloalkyl containing oxygen and/or nitrogen atom(s), and the nitrogen atom in the heterocycloalkyl is optionally substituted with $C_{1-6}$ alkyl;

$R_2$ is selected from the group consisting of halogen and $C_{1-6}$ haloalkyl;

$R_3$ is selected from the group consisting of $C_{1-6}$ alkyl and halogen.

Preferably, the A ring is selected from the group consisting of

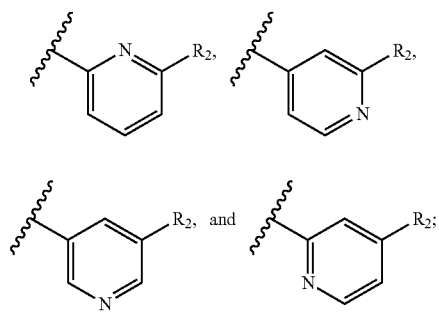

$R_2$ is selected from the group consisting of fluorine, chlorine and trifluoromethyl.

Otherwise preferably, $R_3$ is selected from the group consisting of methyl, fluorine and chlorine.

In one embodiment, the present invention provides a selective PDGFR kinase inhibitor, comprising a compound of formula (Ia) or a pharmaceutically acceptable salt, solvate, ester, acid, metabolite or prodrug thereof:

Formula (Ia)

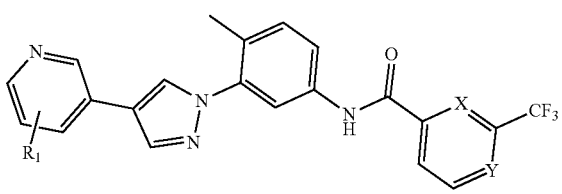

wherein, $R_1$ is selected from the group consisting of heterocycloalkyl, heterocycloalkyloxy, heterocycloalkyl $C_{1-6}$ alkoxy, heterocycloalkylamino, heterospirocycloalkyl, heterospirocycloalkylamino, $C_{3-6}$ cycloalkyl $C_{1-6}$ alkoxy, $C_{3-6}$ cycloalkyloxy, wherein the heterocycloalkyl is optionally substituted with $C_{1-6}$ alkyl;

one of Y and Z is CH and the other is N.

In a preferred embodiment, the "heterocycloalkyl" as described above is preferably a 4- to 6-membered heterocycloalkyl containing oxygen and/or nitrogen atom(s), such as, pyrrolidinyl, morpholinyl, piperazinyl, tetrahydropyranyl, tetrahydrofuranyl, oxetanyl, azetidinyl, and the like, and the nitrogen atom in those heterocycloalkyl groups is optionally substituted with a $C_{1-6}$ alkyl. The "heterospirocycloalkyl" as described above is preferably a 6- to 10-membered spirocycloalkyl group containing oxygen and/or nitrogen heteroatom(s).

In a preferred embodiment, $R_1$ is selected from the group consisting of $C_{1-6}$ alkyl piperazinyl (such as, N-methyl piperazinyl, e.g., 4-methyl-piperazin-1-yl), morpholinyl (such as, N-morpholinyl), tetrahydropyranyl $C_{1-6}$ alkoxy (such as, tetrahydropyran-4-yl methoxy), oxetanyloxy (such as, oxetan-3-yloxy), morpholino $C_{1-6}$ alkoxy (such as, 2-morpholinoethoxy), tetrahydrofuranyl $C_{1-6}$ alkoxy (such as, tetrahydrofuran-2-yl methoxy), $C_{3-6}$ cycloalkyl $C_{1-6}$ alkoxy (such as, cyclopentyl methoxy) and oxa-aza-spiroheptyl (such as, 2-oxa-6-aza-spiro[3.3]hept-6-yl).

In another preferred embodiment, the substituent of $R_1$ is substituted on the carbon atom at a para- or meta-position of the N atom in the pyridine ring, and more preferably, is substituted on the carbon atom at a meta-position of the N atom in the pyridine ring.

In a preferred embodiment, the PDGFR kinase inhibitor of the present invention is selected from the group consisting of the compounds as follows or pharmaceutically acceptable salts thereof:

| Compound No. | Compound Structure |
|---|---|
| 1 | 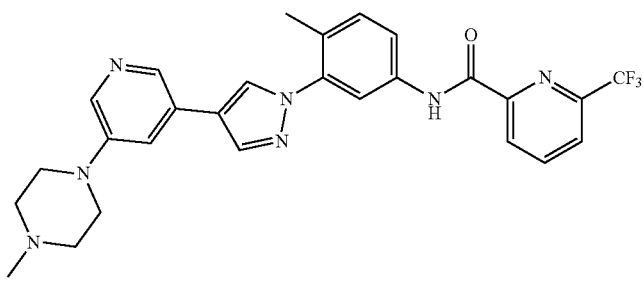 [SMILES: Cc1ccc(NC(=O)c2cccc(C(F)(F)F)n2)cc1-n1cc(-c2cncc(N3CCN(C)CC3)c2)cn1] |
| 2 | 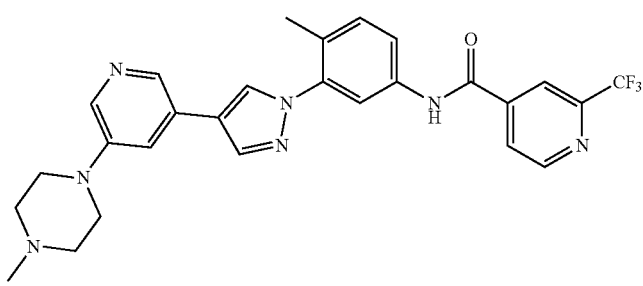 [SMILES: Cc1ccc(NC(=O)c2ccnc(C(F)(F)F)c2)cc1-n1cc(-c2cncc(N3CCN(C)CC3)c2)cn1] |
| 3 | 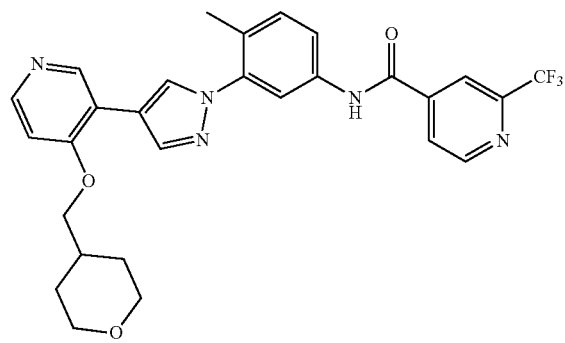 [SMILES: Cc1ccc(NC(=O)c2ccnc(C(F)(F)F)c2)cc1-n1cc(-c2cnccc2OCC2CCOCC2)cn1] |
| 4 | 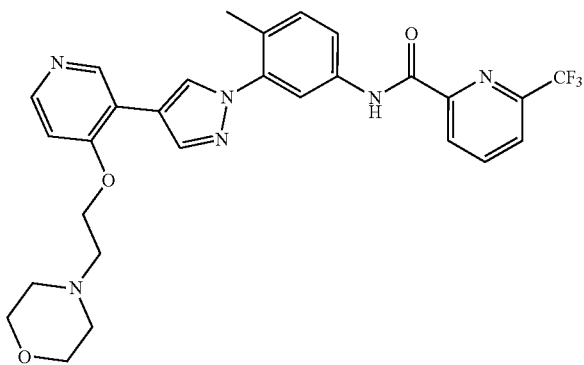 [SMILES: Cc1ccc(NC(=O)c2cccc(C(F)(F)F)n2)cc1-n1cc(-c2cnccc2OCCN2CCOCC2)cn1] |

-continued

| Compound No. | Compound Structure |
|---|---|
| 5 | 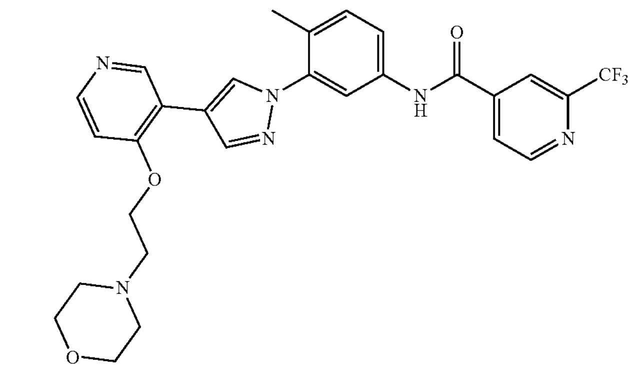 [SMILES: Cc1ccc(NC(=O)c2ccnc(C(F)(F)F)c2)cc1-n1cc(-c2cnccc2OCCN2CCOCC2)cn1] |
| 6 | 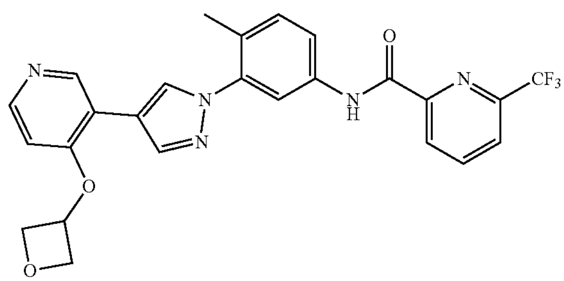 [SMILES: Cc1ccc(NC(=O)c2cccc(C(F)(F)F)n2)cc1-n1cc(-c2cnccc2OC2COC2)cn1] |
| 7 | 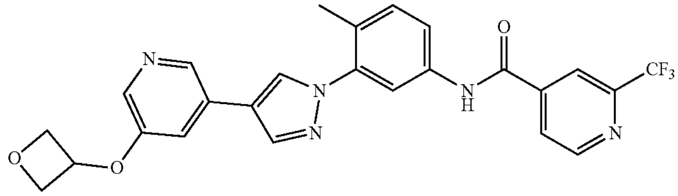 [SMILES: Cc1ccc(NC(=O)c2ccnc(C(F)(F)F)c2)cc1-n1cc(-c2cncc(OC3COC3)c2)cn1] |
| 8 | 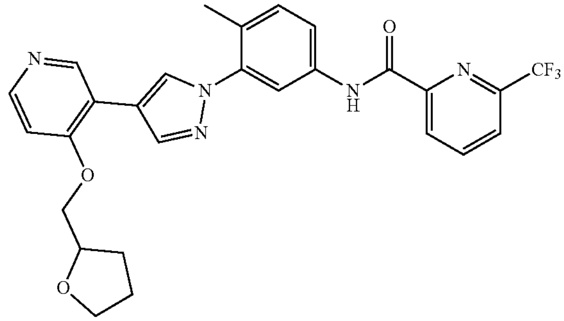 [SMILES: Cc1ccc(NC(=O)c2cccc(C(F)(F)F)n2)cc1-n1cc(-c2cnccc2OCC2CCCO2)cn1] |
| 9 | 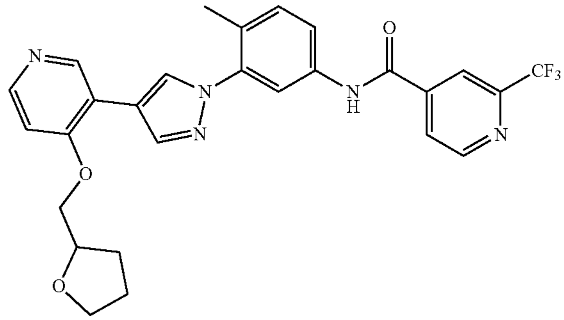 [SMILES: Cc1ccc(NC(=O)c2ccnc(C(F)(F)F)c2)cc1-n1cc(-c2cnccc2OCC2CCCO2)cn1] |

-continued
| Compound No. | Compound Structure |
|---|---|
| 10 | 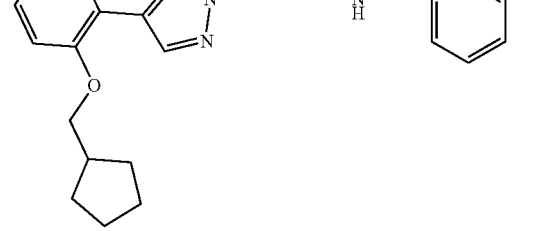 |
| 11 | 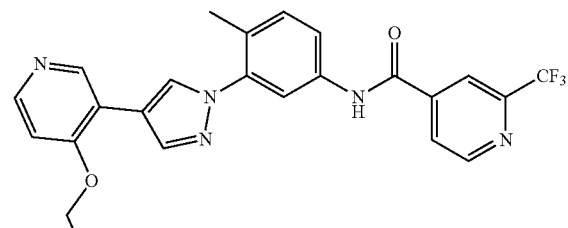 |
| 12 | 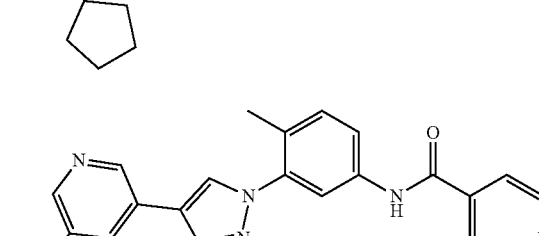 |
| 13 | 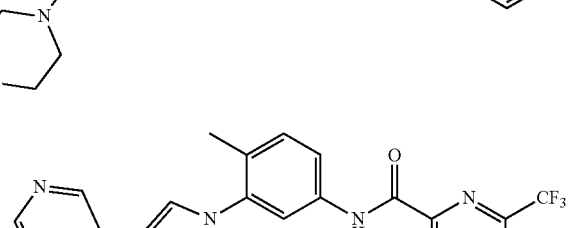 |
| 14 | 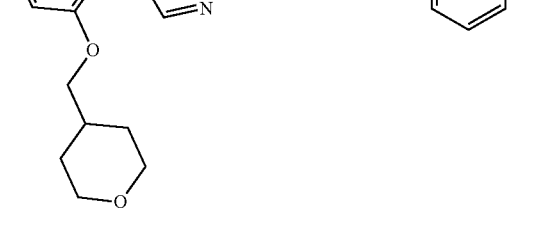 |

-continued

| Compound No. | Compound Structure |
|---|---|
| 15 | 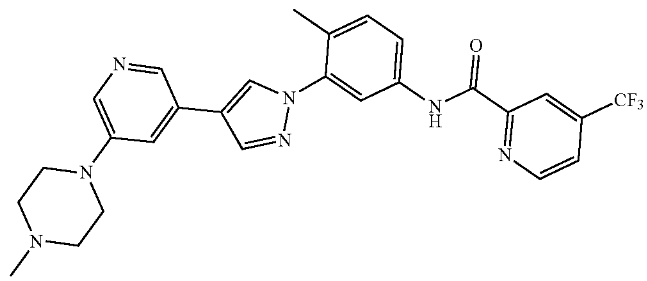 [SMILES: Cc1ccc(NC(=O)c2cc(C(F)(F)F)ccn2)cc1-n1cc(-c2cncc(N3CCN(C)CC3)c2)cn1] |
| 16 | 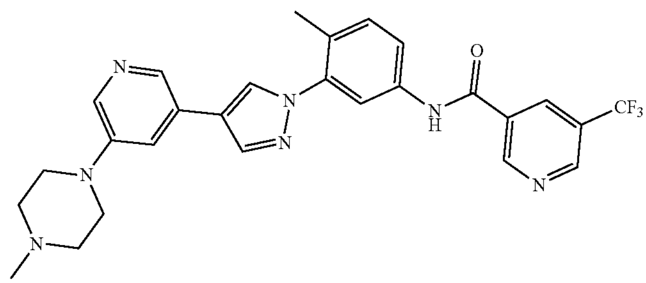 [SMILES: Cc1ccc(NC(=O)c2cncc(C(F)(F)F)c2)cc1-n1cc(-c2cncc(N3CCN(C)CC3)c2)cn1] |
| 17 | 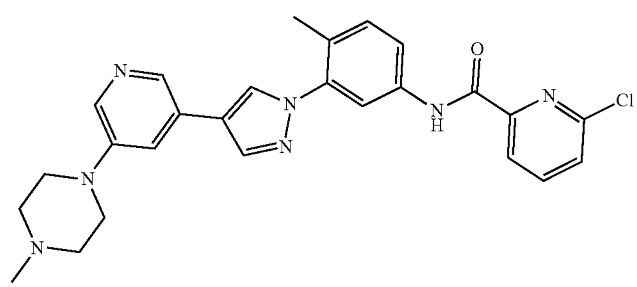 [SMILES: Cc1ccc(NC(=O)c2cccc(Cl)n2)cc1-n1cc(-c2cncc(N3CCN(C)CC3)c2)cn1] |
| 18 | 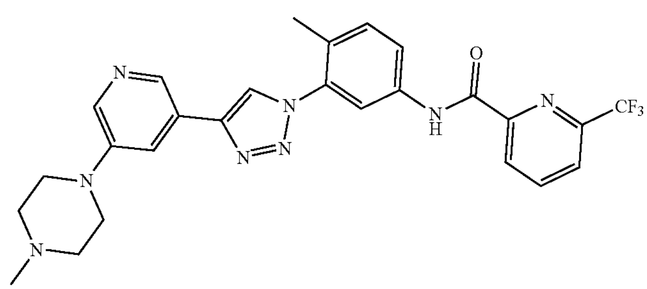 [SMILES: Cc1ccc(NC(=O)c2cccc(C(F)(F)F)n2)cc1-n1cc(-c2cncc(N3CCN(C)CC3)c2)nn1] |
| 19 | 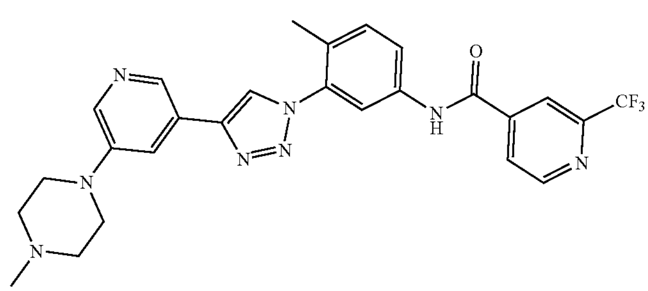 [SMILES: Cc1ccc(NC(=O)c2ccnc(C(F)(F)F)c2)cc1-n1cc(-c2cncc(N3CCN(C)CC3)c2)nn1] |

| Compound No. | Compound Structure |
|---|---|
| 20 | 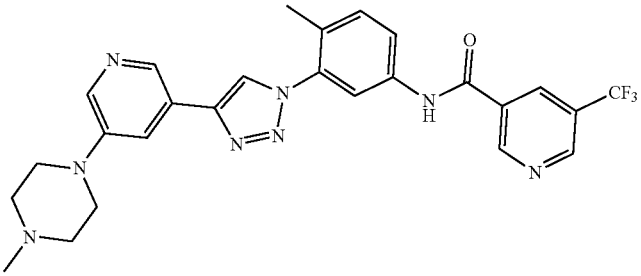 [SMILES: Cc1ccc(NC(=O)c2cncc(C(F)(F)F)c2)cc1-n1cc(-c2cncc(N3CCN(C)CC3)c2)nn1] |
| 21 | 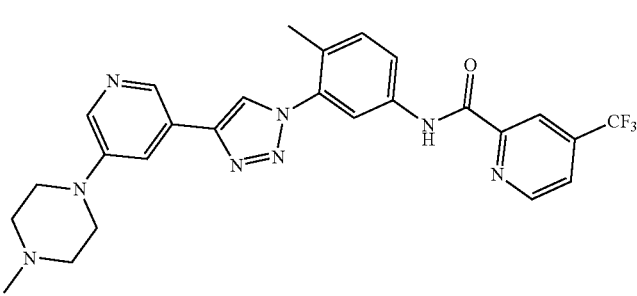 [SMILES: Cc1ccc(NC(=O)c2cc(C(F)(F)F)ccn2)cc1-n1cc(-c2cncc(N3CCN(C)CC3)c2)nn1] |
| 22 | 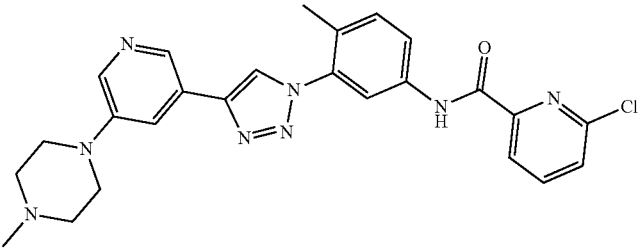 [SMILES: Cc1ccc(NC(=O)c2cccc(Cl)n2)cc1-n1cc(-c2cncc(N3CCN(C)CC3)c2)nn1] |
| 23 | 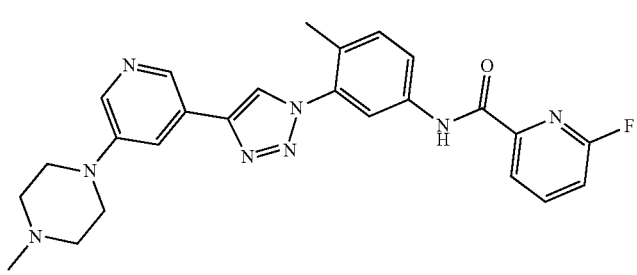 [SMILES: Cc1ccc(NC(=O)c2cccc(F)n2)cc1-n1cc(-c2cncc(N3CCN(C)CC3)c2)nn1] |
| 24 | 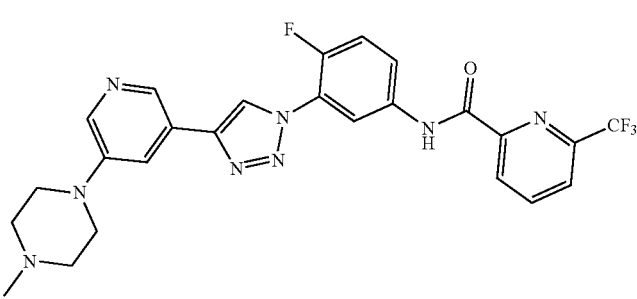 [SMILES: CN1CCN(c2cncc(-c3cn(-c4cc(NC(=O)c5cccc(C(F)(F)F)n5)ccc4F)nn3)c2)CC1] |

-continued

| Compound No. | Compound Structure |
|---|---|
| 25 | 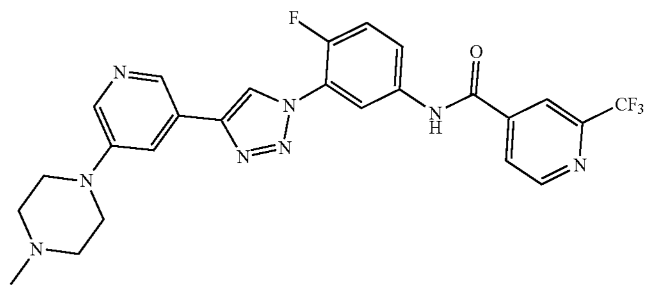 [SMILES: CN1CCN(c2cncc(-c3cn(-c4cc(NC(=O)c5ccnc(C(F)(F)F)c5)ccc4F)nn3)c2)CC1] |
| 26 | 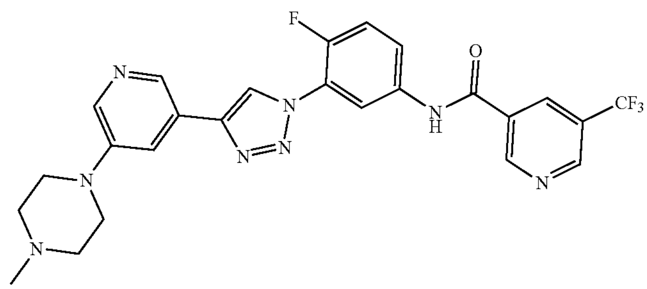 [SMILES: CN1CCN(c2cncc(-c3cn(-c4cc(NC(=O)c5cncc(C(F)(F)F)c5)ccc4F)nn3)c2)CC1] |
| 27 | 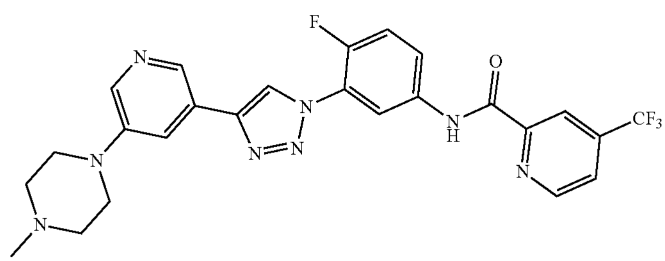 [SMILES: CN1CCN(c2cncc(-c3cn(-c4cc(NC(=O)c5cc(C(F)(F)F)ccn5)ccc4F)nn3)c2)CC1] |
| 28 | 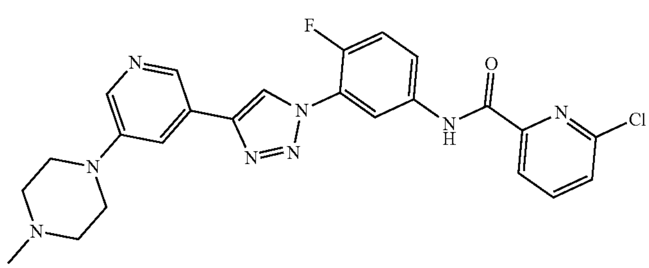 [SMILES: CN1CCN(c2cncc(-c3cn(-c4cc(NC(=O)c5cccc(Cl)n5)ccc4F)nn3)c2)CC1] |
| 29 | 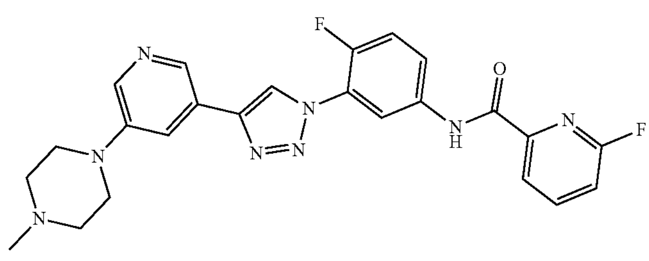 [SMILES: CN1CCN(c2cncc(-c3cn(-c4cc(NC(=O)c5cccc(F)n5)ccc4F)nn3)c2)CC1] |

-continued
| Compound No. | Compound Structure |
|---|---|
| 30 | 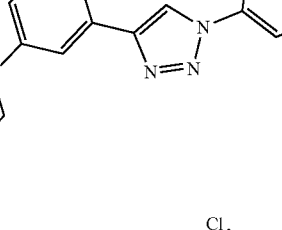 |
| 31 | 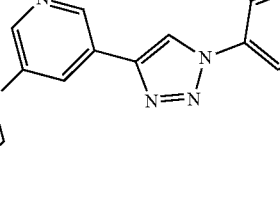 |
| 32 | 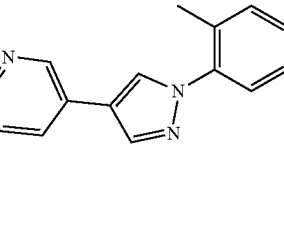 |
| 33 | 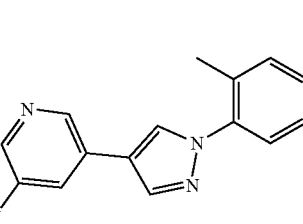 |
| 34 | 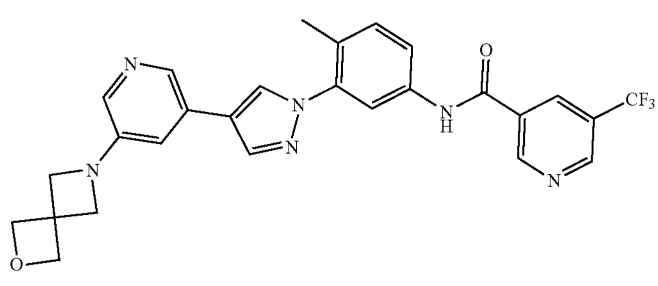 [SMILES: Cc1ccc(NC(=O)c2cncc(C(F)(F)F)c2)cc1-n1cc(-c2cncc(N3CC4(COC4)C3)c2)cn1] |

| Compound No. | Compound Structure |
|---|---|
| 35 | 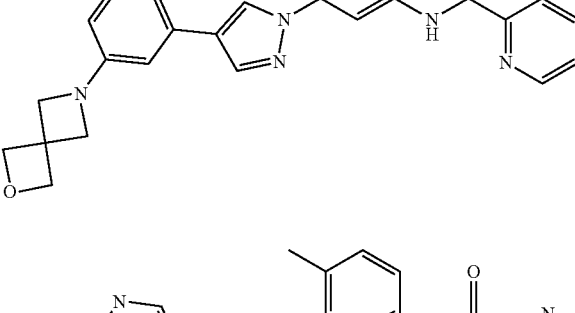 |
| 36 | 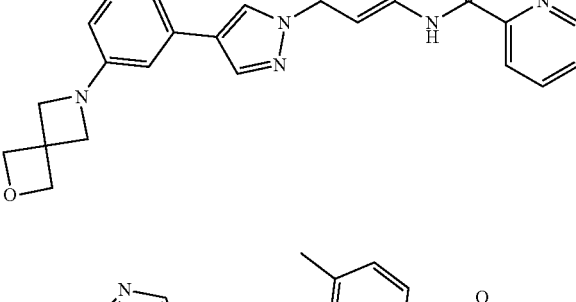 |
| 37 | 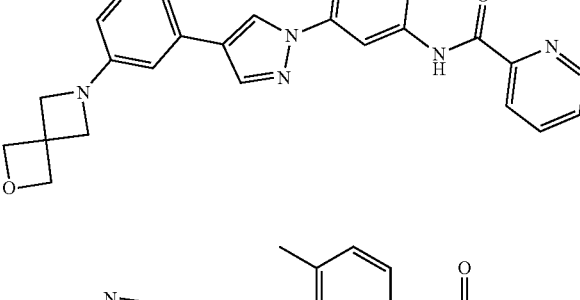 |
| 38 | 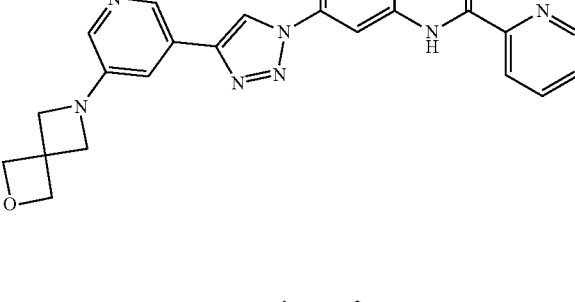 |
| 39 | 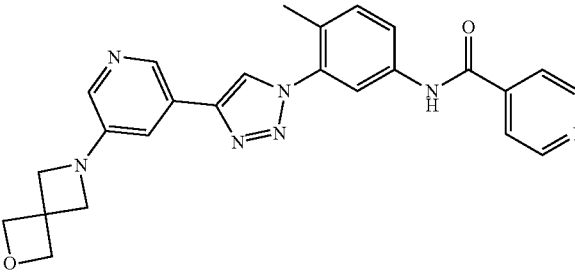 |

| Compound No. | Compound Structure |
|---|---|
| 40 | 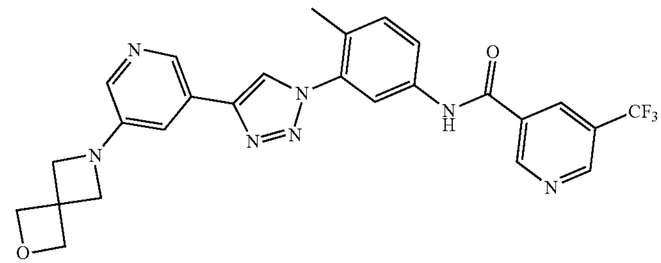 [SMILES: Cc1ccc(NC(=O)c2cncc(C(F)(F)F)c2)cc1-n1cc(-c2cncc(N3CC4(COC4)C3)c2)nn1] |
| 41 | 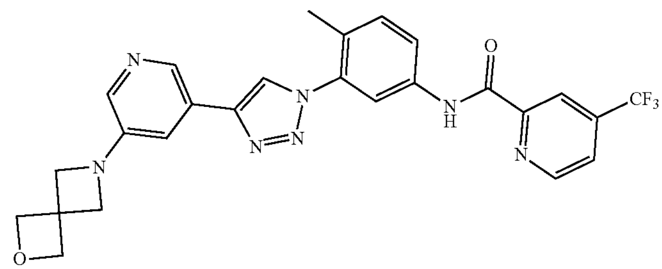 [SMILES: Cc1ccc(NC(=O)c2cc(C(F)(F)F)ccn2)cc1-n1cc(-c2cncc(N3CC4(COC4)C3)c2)nn1] |
| 42 | 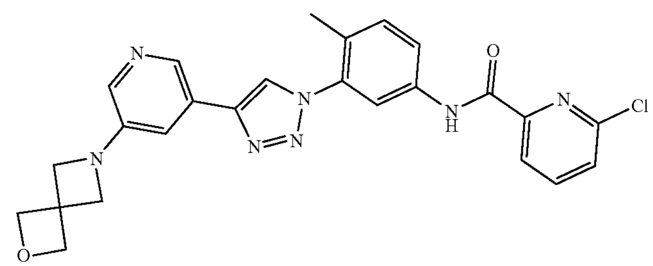 [SMILES: Cc1ccc(NC(=O)c2cccc(Cl)n2)cc1-n1cc(-c2cncc(N3CC4(COC4)C3)c2)nn1] |
| 43 | 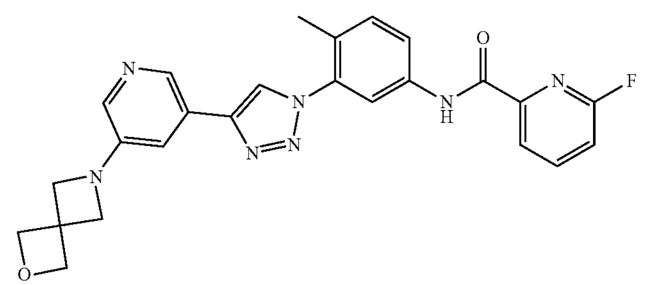 [SMILES: Cc1ccc(NC(=O)c2cccc(F)n2)cc1-n1cc(-c2cncc(N3CC4(COC4)C3)c2)nn1] |

Any combination of the groups described above for the various variables is contemplated herein. It is understood that substituents and substitution patterns on the compounds provided herein may be selected by one of ordinary skill in the art to provide chemically stable compounds that can be synthesized by techniques known in the art, as well as those set forth herein.

Described herein is a novel kinase inhibitor. The pharmaceutically acceptable salts, solvates, esters, acids, pharmaceutically active metabolites and prodrugs of these compounds are also described herein.

In additional or further embodiments, the compound described herein is metabolized upon administration to an organism in need thereof to produce a metabolite that is then used to produce a desirable effect, including a desirable therapeutic effect.

The compound described herein may be formed as, and/or used as, a pharmaceutically acceptable salt. Types of the pharmaceutical acceptable salt, include, but are not limited to: (1) acid addition salts, formed by reacting the compound in a form of free base with a pharmaceutically acceptable inorganic acid such as hydrochloric acid, hydrobromic acid, sulfuric acid, nitric acid, phosphoric acid, metaphosphoric acid, or the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2]oct-2-ene-1-carboxylic acid, 2-naphthalenesulfonic acid, tert-butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, or the like; (2) base addition salts formed when an acidic proton present in the parent compound either is replaced by a metal ion such as an alkali metal ion (such as, lithium, sodium, potassium), an alkaline earth metal ion (such as, magnesium, or calcium), or an aluminum ion; or coordinates with an organic base or an inorganic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

Corresponding counterions of the pharmaceutically acceptable salt may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by utilizing at least one of the following techniques: filtration, precipitation with a non-solvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, X-ray diffraction, spectroscopy, microscopy, and element analysis. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition of the Present Invention

The present application also provides a pharmaceutical composition comprising at least one compound of formula (I), or a pharmaceutically acceptable salt, solvate, ester, acid, pharmaceutically active metabolite or prodrug of the compound, and a pharmaceutically acceptable carrier or excipient, and optionally other therapeutic agent.

In the course of treatment, it may be used alone or in combination with one or more other therapeutic agents. The medicament comprising a compound of the present invention may be administered to a patient through at least one of injection, oral, inhalation, rectal and transdermal administration. Other therapeutic agents may be selected from the group consisting of immunosuppressants (such as, tacrolimus, cyclosporin, rapamycin, methotrexate, cyclophosphamide, azathioprine, mercaptopurine, mycophenolate, or FTY720), glucocorticoids (such as, prednisone, cortisone acetate, prednisolone, methylprednisolone, dexamethasone, betamethasone, triamcinolone, fluorohydroxyprednisolone, beclomethasone, fluohydrocortisone acetate, deoxycorticosterone acetate, aldosterone), non-steroidal anti-inflammatory agents (such as, salicylates, arylalkanoic acids, 2-arylpropionic acids, N-arylanthranilic acids, oxicams, coxibs, or sulphonanilides), allergy vaccines, antihistamines, antileukotrienes, β-agonists, theophylline, anticholinergics, or other selective kinase inhibitors (such as, mTOR inhibitors, c-Met inhibitors) or her2 antibody agents. In addition, the referenced other therapeutic agents may also be Rapamycin, Crizotinib, Tamoxifen, Raloxifene, Anastrozole, Exemestane, Letrozole, Herceptin™ (Trastuzumab), Gleevec™ (Imatinib mesylate), Taxol™ (Paclitaxel), Cyclophosphamide, Lovastatin, Minosine, Cytarabine, 5-Fluorouracil (5-FU), Methotrexate (MTX), Taxotere™ (Docetaxel), Zoladex™ (Goserelin), Vincristine, Vinblastine, Nocodazole, Teniposide, Etoposide, Gemzar™ (Gemcitabine), Epothilone, Navelbine, Camptothecin, Daunonibicin, Dactinomycin, Mitoxantrone, Amsacrine, Doxorubicin (Adriamycin), Epirubicin or Idarubicin. Alternatively, other therapeutic agents may be, for example, but not limited to, cytokines such as G-CSF (Granulocyte-Colony Stimulating Factor). Alternatively, other therapeutic agents may be for example, but are not limited to, CMF (Cyclophosphamide, Methotrexate and 5-Fluorouracil), CAF (Cyclophosphamide, Adriamycin and 5-Fluorouracil), AC (Adriamycin and Cyclophosphamide), FEC (5-Fluorouracil, Epirubicin and Cyclophosphamide), ACT or ATC (Adriamycin, Cyclophosphamide and Paclitaxel) or CMFP (Cyclophosphamide, Methotrexate, 5-Fluorouracil and Prednisone).

In embodiments of the present invention, when a patient is treated in accordance with the present invention, the amount of a given agent will vary depending upon factors such as the particular dosing regimen, the type of the disease or condition and its severity, the identity (e.g., body weight) of the subject or host in need of treatment, but can be routinely determined in a manner known in the art according to the particular circumstances, including, e.g., the specific agent being administered, the route of administration, the condition being treated, and the subject or host being treated. In general, doses employed for adult human treatment will typically be in a range of 0.02-5000 mg per day, such as, about 1-1500 mg per day. The desirable dose may conveniently be presented as a single dose or as divided doses administered simultaneously (or over a short period of time) or at appropriate intervals, for example, as two, three, four or more sub-doses per day. It will be appreciated by those skilled in the art that, although the above dosage ranges are given, the specific effective amounts may be appropriately adjusted depending on the condition of the patient and the judgment of the practitioner.

Use of Medicaments of the Present Invention

The compound or a pharmaceutically acceptable salt, solvate, ester, acid, metabolite or prodrug thereof, or the pharmaceutical composition of the present invention is capable of selectively inhibiting the activity of PDGFR tyrosine kinase (wild-type or various mutants or a combination thereof), especially the activity of PDGFRα and PDGFRβ, and more especially, the activity of PDGFRα. The compound or a pharmaceutically acceptable salt, solvate, ester, acid, metabolite or prodrug thereof, or the pharmaceutical composition of the present invention is useful in the treatment, prevention or amelioration of one or more diseases, disorders or conditions which are modulated or affected by, or involved in the activity of PDGFR (especially PDGFRα and PDGFRβ), such as, a disease selected from the group consisting of pulmonary hypertension, solid tumors (including benign or malignant types), sarcoma, gastrointestinal stromal tumors (GIST), colon cancer, acute myeloblastic leukemia (AML), chronic myelogenous leukemia (CML), neoplasia, thyroid carcinoma, systemic mastocytosis, eosinophilia syndrome, chronic eosinophilic leukemia, fibrosis, lupus erythematosus, graft versus host disease, neurofibromatosis, pulmonary hypertension, Alzheimer's disease, seminoma, dysgerminoma, mast cell tumors, lung cancer, bronchial carcinoma, testicular intraepithelial neoplasia, melanoma, breast cancer, neuroblastoma, papillary/follicular thyroid carcinoma, malignant lymphoma, non-Hodgkin's lymphoma, multiple endocrine neoplasia type 2, pheochromocytoma, thyroid carcinoma, parathyroid hyperplasia/adenoma, colon cancer, colorectal adenoma, ovarian cancer, prostate cancer, glioblastoma, brain tumor, malignant glioma, pancreatic cancer, malignant pleural mesothelioma, hemangioblastoma, hemangioma, kidney cancer, liver cancer, adrenal carcinoma, bladder cancer, gastric cancer, rectal cancer, vaginal cancer, cervical cancer, endometrial cancer, multiple myeloma, neck and head tumors, as well as other proliferative conditions, or the like, or a combination thereof. It is especially preferred for the treatment of pulmonary hypertension, chronic eosinophilic leukemia, or the like or a combination thereof.

The compound or a pharmaceutically acceptable salt, solvate, ester, acid, metabolite or prodrug thereof, or the pharmaceutical composition of the present invention is useful in the treatment, prevention or amelioration of an autoimmune disease selected from the group consisting of arthritis, rheumatic arthritis, lupus, rheumatoid arthritis, inflammatory bowel disease, psoriatic arthritis, osteoarthritis, Still's disease, juvenile arthritis, diabetes, myasthenia gravis, Hashimoto's thyroiditis, Ord's thyroiditis, Graves' disease, Sjögren's syndrome, multiple sclerosis, Guillain-Barré syndrome, acute disseminated encephalomyelitis, Addison's disease, opsoclonus-myoclonus syndrome, ankylosing spondylitis, antiphospholipid antibody syndrome, aplastic anemia, autoimmune hepatitis, coeliac disease, Goodpasture's syndrome, idiopathic thrombocytopeniaurpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, vulvodynia, or a combination thereof.

Preparation of the Compound.

The compound of the present invention may be synthesized using standard synthetic techniques known to those of skill in the art or using methods known in the art in combination with methods described herein. In additions, solvents, temperatures and other reaction conditions presented herein may be varied according to techniques in the art. As a further guide the following synthetic methods may also be utilized.

The reactions as described can be employed in sequence to provide the compounds described herein or they may be used to synthesize building blocks which are subsequently joined by the methods described herein and/or known in the art.

In certain embodiments, provided herein are methods of preparing and methods of using tyrosine kinase inhibitor compounds described herein. In certain embodiments, the compounds described herein can be synthesized through the following synthetic schemes. The compounds may be synthesized using methodologies similar to those described below by the use of appropriate alternative starting materials.

The starting materials used for synthesis of the compounds described herein may be synthesized or can be commercially obtained. The compounds described herein and other related compounds having different substituents can be synthesized using techniques and materials known to those of skill in the art. General methods for the preparation of compounds as disclosed herein may be derived from known reactions in the field, and the reactions may be modified by the use of appropriate reagents and conditions, as would be recognized by the skilled person, for the introduction of the various moieties into the molecules as provided herein.

The reaction products may be isolated and purified, if desired, using conventional techniques, including, but not limited to, filtration, distillation, crystallization, chromatography and the like. Such products may be characterized using conventional means, including physical constants and spectral data.

Example 1

Synthesis of N-(4-methyl-3-(4-(5-(4-methylpiperazin-1-yl)pyridin-3-yl)-1H-pyrazol-1-yl)phenyl)-6-(trifluoromethyl)picolinamide 1

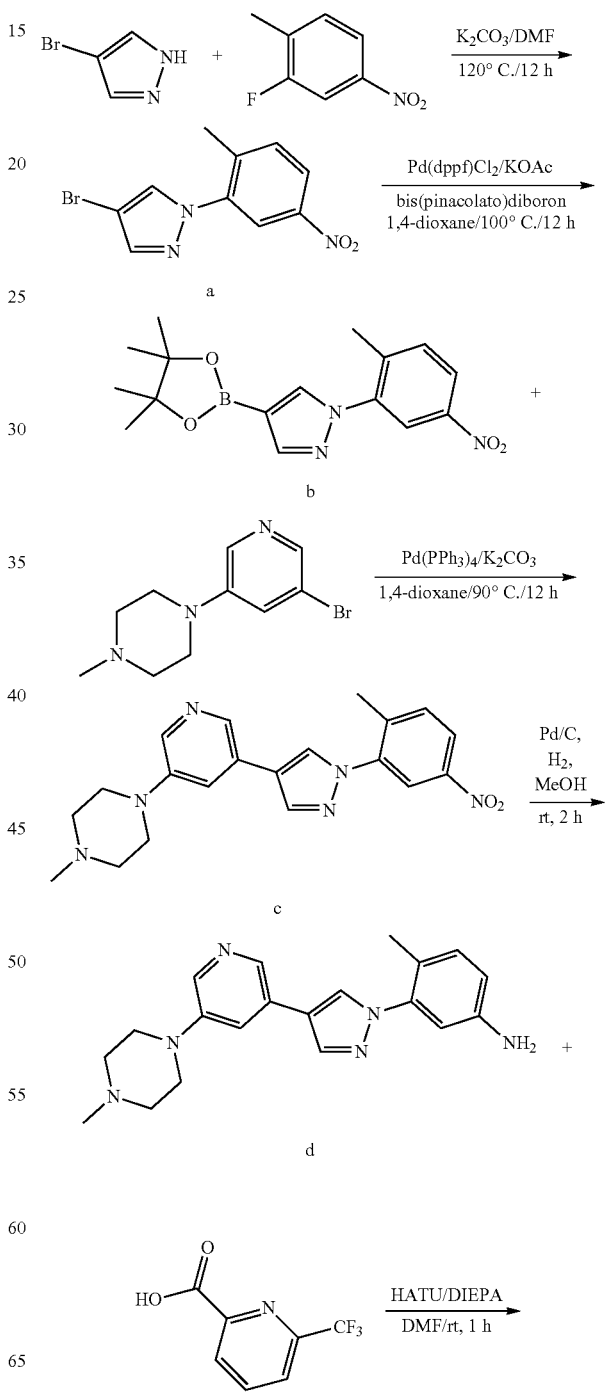

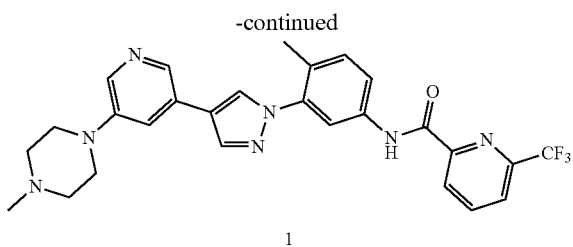

1

Step 1. Synthesis of the compound of 4-bromo-1-(2-methyl-5-nitrophenyl)-1H-pyrazole a The compounds of 4-bromopyrazole (5 g, 1 eq), 2-fluoro-1-methyl-4-nitrobenzene (5.5 g, 1.05 eq) and potassium carbonate (13.1, 3 eq) were mixed in DMF (50 ml). The mixture was stirred overnight at 120° C. in a nitrogen atmosphere, then cooled and concentrated. Ethyl acetate (200 ml) was added into the concentrate. Thereafter, the resultant mixture was washed with water and saturated brine sequentially, dried over anhydrous sodium sulfate, and filtered. The filtrate was concentrated, and then subjected to column chromatography to give a yellow product a (5.2 g).

Step 2. Synthesis of the compound of 1-(2-methyl-5-nitrophenyl)-4-(4,4,5,5-tetramethyl-1,3,2-dioxaborolan-2-yl)-1H-pyrazole b The compound a (5 g, 1 eq), bis (pinacolato)diboron (5.8 g, 1.3 eq), potassium acetate (3.5 g, 2 eq), and [1,1'-bis (diphenylphosphino) ferrocene] palladium dichloride (0.72 g, 0.05 eq) were mixed in 1,4-dioxane (50 mL). The mixture was stirred overnight at 100° C. in a nitrogen atmosphere, and then concentrated. The concentrate was subjected to column chromatography to give a yellow product b (4.0 g).

Step 3. Synthesis of 1-methyl-4-(5-(1-(2-methyl-5-nitrophenyl)-1H-pyrazol-4-yl)pyridin-3-yl)piperazine c The compound b (4.0 g, 1.1 eq), 1-(5-bromopyridin-3-yl)-4-methylpiperazine (2.8 g, 1 eq), potassium carbonate (3.0 g, 2 eq) and tetrakis(triphenylphosphine) palladium (0.6 g, 0.05 eq) were mixed in 1,4-dioxane (40 mL) and water (4 mL). The mixture was stirred overnight at 90° C. in a nitrogen atmosphere, and then concentrated. The concentrate was subjected to column chromatography to give a yellow product c (3.8 g).

Step 4. Synthesis of 4-methyl-3-(4-(5-(4-methylpiperazin-1-yl)pyridin-3-yl)-1H-pyrazol-1-yl) aniline d The compound c (2.8 g, 1 eq) and palladium on carbon (0.5 g) were mixed in methanol (30 mL). The mixture was stirred for 2 hours at room temperature in a hydrogen atmosphere. Thereafter, dichloromethane (100 mL) was added to dilute the mixture. The resultant mixture was filtered, and concentrated to give a pale green product d (2.1 g).

Step 5. Synthesis of the compound of N-(4-methyl-3-(4-(5-(4-methylpiperazin-1-yl)pyridin-3-yl)-1H-pyrazol-1-yl)phenyl)-6-(trifluoromethyl)picolinamide 1

The compound d (0.05 g, 1 eq), 6-(trifluoromethyl)pyridine-2-carboxylic acid (0.27 g, 1 eq), 2-(7-azabenzotriazole)-N,N,N',N'-tetramethyluronium hexafluorophosphate HATU (0.072 g, 1.1 eq), and diisopropylethylenediamine (DIEPA) (0.22 g, 1 eq) were mixed in N,N-dimethylformamide DMF (2 ml). The mixture was stirred at room temperature for 1 hour. Thereafter, ethyl acetate (50 mL) was added to dilute the mixture. The mixture was washed with water and saturated brine sequentially, dried over anhydrous sodium sulfate, and filtered. The filtrate was concentrated to give a product 1 (0.07 g). Exact Mass (calculated): 521.21; MS (ESI) m/z (M+1)$^+$: 522.21.

Example 2

Synthesis of N-(4-methyl-3-(4-(5-(4-methylpiperazin-1-yl)pyridin-3-yl)-1H-pyrazol-1-yl)phenyl)-2-(trifluoromethyl)isonicotinamide 2

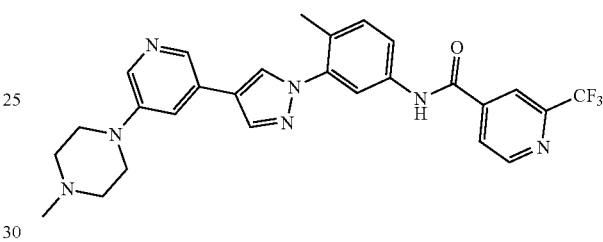

Compound 2 was synthesized by employing steps similar to those described in Example 1. Exact Mass (calculated): 521.21; MS (ESI) m/z (M+1)+: 522.21.

Example 3

Synthesis of N-(4-methyl-3-(4-(4-((tetrahydropyran-4-yl) methoxy) pyridin-3-yl)-1H-pyrazol-1-yl)phenyl)-2-(trifluoromethyl)isonicotinamide 3

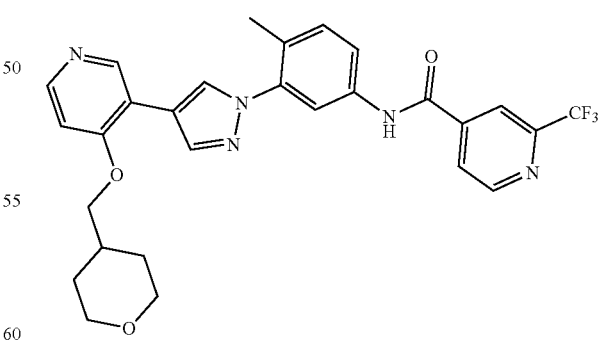

Compound 3 was synthesized by employing steps similar to those described in Example 1. Exact Mass (calculated): 537.19; MS (ESI) m/z (M+1)+: 538.19.

Example 4

Synthesis of N-(4-methyl-3-(4-(4-(2-morpholinoethoxy) pyridin-3-yl)-1H-pyrazol-1-yl)phenyl)-6-(trifluoromethyl)picolinamide 4

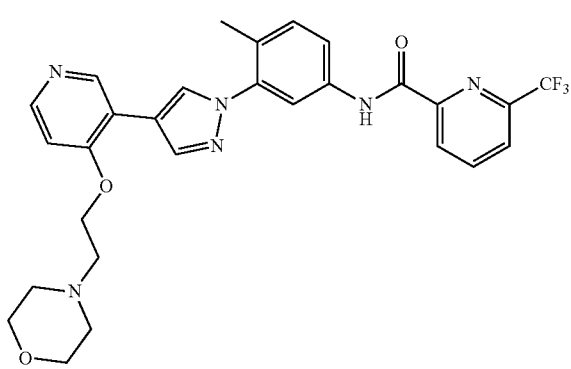 [SMILES: Cc1ccc(NC(=O)c2cccc(C(F)(F)F)n2)cc1-n1cc(-c2cnccc2OCCN2CCOCC2)cn1]

Compound 4 was synthesized by employing steps similar to those described in Example 1. Exact Mass (calculated): 552.20; MS (ESI) m/z (M+1)+: 553.20.

Example 5

Synthesis of N-(4-methyl-3-(4-(4-(2-morpholinoethoxy) pyridin-3-yl)-1H-pyrazol-1-yl)phenyl)-2-(trifluoromethyl)isonicotinamide 5

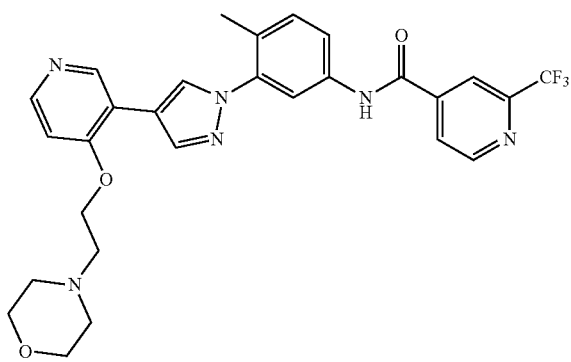 [SMILES: Cc1ccc(NC(=O)c2ccnc(C(F)(F)F)c2)cc1-n1cc(-c2cnccc2OCCN2CCOCC2)cn1]

Compound 5 was synthesized by employing steps similar to those described in Example 1. Exact Mass (calculated): 552.20; MS (ESI) m/z (M+1)+: 553.20.

Example 6

Synthesis of N-(4-methyl-3-(4-(4-(oxetan-3-yloxy) pyridin-3-yl)-1H-pyrazol-1-yl)phenyl)-6-(trifluoromethyl)picolinamide 6

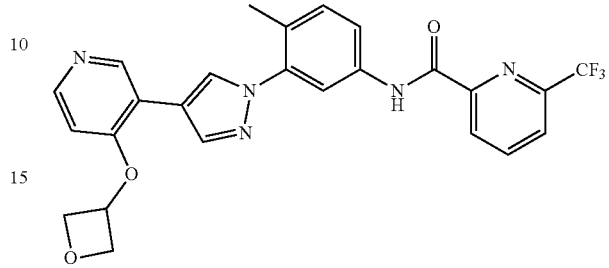

Compound 6 was synthesized by employing steps similar to those described in Example 1. Exact Mass (calculated): 495.15; MS (ESI) m/z (M+1)+: 496.15.

Example 7

Synthesis of N-(4-methyl-3-(4-(5-(oxetan-3-yloxy) pyridin-3-yl)-1H-pyrazol-1-yl)phenyl)-2-(trifluoromethyl)isonicotinamide 7

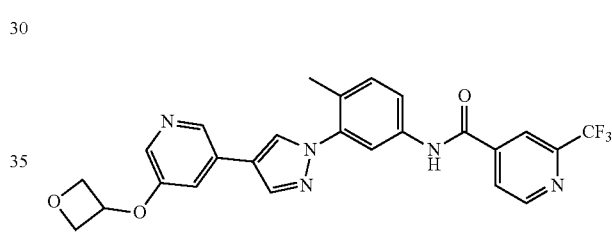

Compound 7 was synthesized by employing steps similar to those described in Example 1. Exact Mass (calculated): 495.15; MS (ESI) m/z (M+1)+: 496.15.

Example 8

Synthesis of N-(4-methyl-3-(4-(4-((tetrahydrofuran-2-yl) methoxy) pyridin-3-yl)-1H-pyrazol-1-yl)phenyl)-6-(trifluoromethyl)picolinamide 8

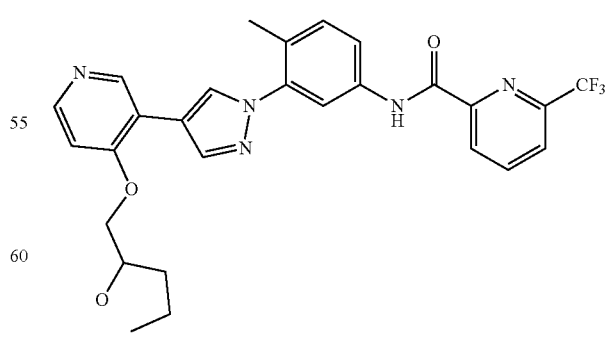

Compound 8 was synthesized by employing steps similar to those described in Example 1. Exact Mass (calculated): 523.18; MS (ESI) m/z (M+1)+: 524.18.

Example 9

Synthesis of N-(4-methyl-3-(4-(4-((tetrahydrofuran-2-yl) methoxy) pyridin-3-yl)-1H-pyrazol-1-yl)phenyl)-2-(trifluoromethyl)isonicotinamide 9

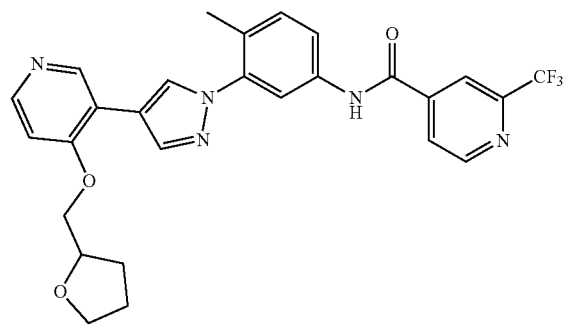 [SMILES: Cc1ccc(NC(=O)c2ccnc(C(F)(F)F)c2)cc1-n1cc(-c2cnccc2OCC2CCCO2)cn1]

Compound 9 was synthesized by employing steps similar to those described in Example 1. Exact Mass (calculated): 523.18; MS (ESI) m/z (M+1)+: 524.18.

Example 10

Synthesis of N-(3-(4-(4-(cyclopentylmethoxy) pyridin-3-yl)-1H-pyrazol-1-yl)-4-methylphenyl)-6-(trifluoromethyl)picolinamide 10

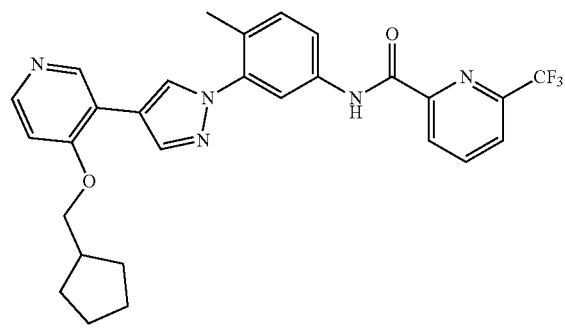 [SMILES: Cc1ccc(NC(=O)c2cccc(C(F)(F)F)n2)cc1-n1cc(-c2cnccc2OCC2CCCC2)cn1]

Compound 10 was synthesized by employing steps similar to those described in Example 1. Exact Mass (calculated): 521.20; MS (ESI) m/z (M+1)+: 522.20.

Example 11

Synthesis of N-(3-(4-(4-(cyclopentylmethoxy) pyridin-3-yl)-1H-pyrazol-1-yl)-4-methylphenyl)-2-(trifluoromethyl)isonicotinamide 11

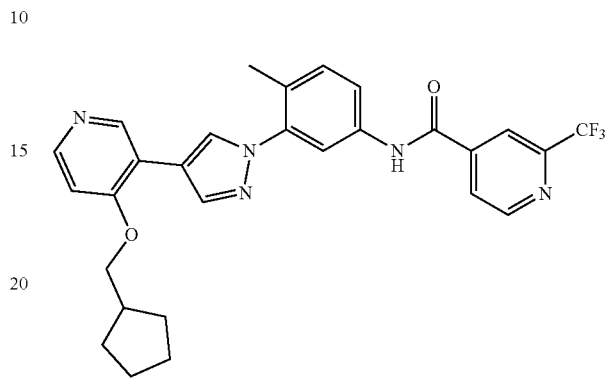

Compound 11 was synthesized by employing steps similar to those described in Example 1. Exact Mass (calculated): 521.20; MS (ESI) m/z (M+1)+: 522.20.

Example 12

Synthesis of N-(4-methyl-3-(4-(5-morpholinopyridin-3-yl)-1H-pyrazol-1-yl)phenyl)-2 (trifluoromethyl)isonicotinamide 12

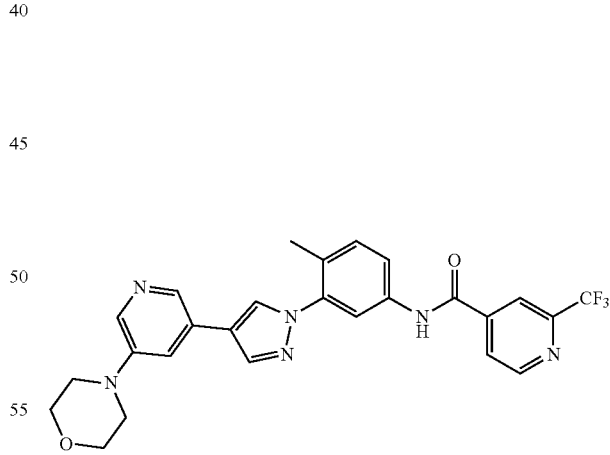

Compound 12 was synthesized by employing steps similar to those described in Example 1. Exact Mass (calculated): 508.18; MS (ESI) m/z (M+1)+: 509.18.

Example 13

Synthesis of N-(4-methyl-3-(4-(4-((tetrahydropyran-4-yl) methoxy) pyridin-3-yl)-1H-pyrazol-1-yl)phenyl)-6-(trifluoromethyl)picolinamide 13

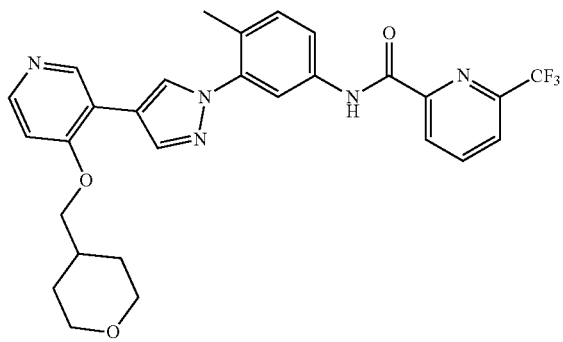 [SMILES: Cc1ccc(NC(=O)c2cccc(C(F)(F)F)n2)cc1-n1cc(-c2cnccc2OCC2CCOCC2)cn1]

Compound 13 was synthesized by employing steps similar to those described in Example 1. Exact Mass (calculated): 537.19; MS (ESI) m/z (M+1)+: 538.19.

Example 14

6-fluoro-N-(4-methyl-3-(4-(5-(4-methylpiperazin-1-yl)pyridin-3-yl)-1H-pyrazol-1-yl)phenyl)picolinamide 14

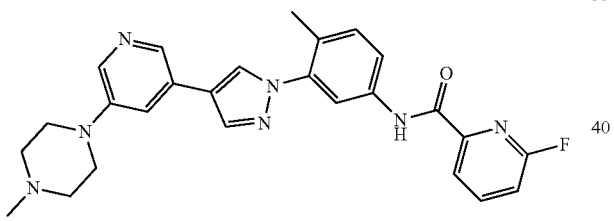

Compound 14 was synthesized by employing steps similar to those described in Example 1. Exact Mass (calculated): 471.21; MS (ESI) m/z (M+1)+: 472.21.

Example 15

N-(4-methyl-3-(4-(5-(4-methylpiperazin-1-yl)pyridin-3-yl)-1H-pyrazol-1-yl)phenyl)-4-(trifluoromethyl)picolinamide 15

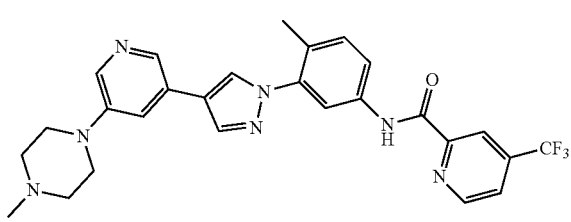 [SMILES: Cc1ccc(NC(=O)c2cc(C(F)(F)F)ccn2)cc1-n1cc(-c2cncc(N3CCN(C)CC3)c2)cn1]

Compound 15 was synthesized by employing steps similar to those described in Example 1. Exact Mass (calculated): 521.21; MS (ESI) m/z (M+1)+: 522.21.

Example 16

N-(4-methyl-3-(4-(5-(4-methylpiperazin-1-yl)pyridin-3-yl)-1H-pyrazol-1-yl)phenyl)-5-(trifluoromethyl)nicotinamide 16

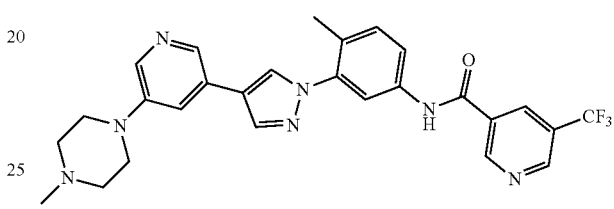

Compound 16 was synthesized by employing steps similar to those described in Example 1. Exact Mass (calculated): 521.21; MS (ESI) m/z (M+1)+: 522.21.

Example 17

6-chloro-N-(4-methyl-3-(4-(5-(4-methylpiperazin-1-yl)pyridin-3-yl)-1H-pyrazol-1-yl)phenyl)picolinamide 17

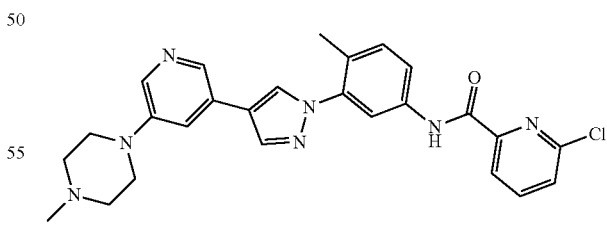

Compound 17 was synthesized by employing steps similar to those described in Example 1. Exact Mass (calculated): 487.18; MS (ESI) m/z (M+1)+: 488.18.

Example 18

Synthesis of (4-methyl-3-(4-(5-(4-methylpiperazin-1-yl)pyridin-3-yl)-1H-1,2,3-triazol-1-yl)phenyl)-6-(trifluoromethyl)picolinamide 18

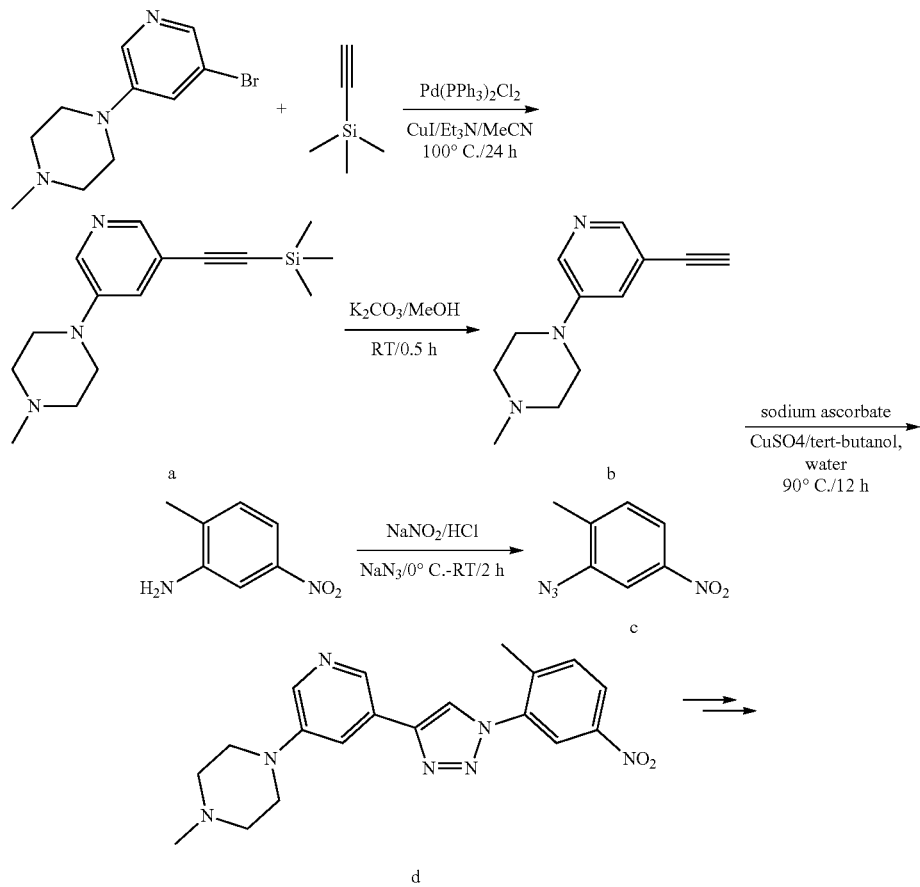

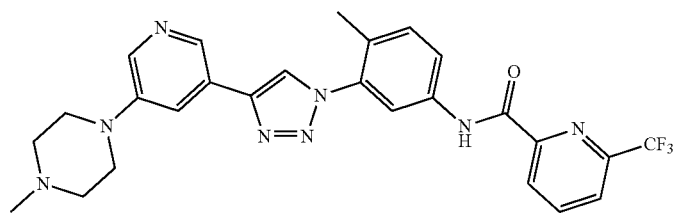

Step 1: Synthesis of 1-methyl-4-(5-(2-(trimethylsilyl) ethynyl)pyridin-3-yl)piperazine a 1-(5-bromopyridin-3-yl)-4-methylpiperazine (5 g, 1 eq), trimethylsilylacetylene (5.7 g, 3 eq), Pd(PPh₃)₂Cl₂ (0.7 g, 0.05 eq), Et₃N (5.9 g, 3 eq), CuI (0.18 g, 0.05 eq) and acetonitrile (50 mL) were mixed. The mixture was stirred for 24 hours at 100° C. at the protection of nitrogen gas, and then cooled. The solid was filtered off. The filtrate was concentrated, and subjected to column chromatography to give a brown solid a (4.5 g).

Step 2: Synthesis of 1-(5-ethynylpyridin-3-yl)-4-methylpiperazine b 1-methyl-4-(5-(2-(trimethylsilyl) ethynyl)pyridin-3-yl) piperazine a (4 g, 1 eq), K₂CO₃ (4 g, 2 eq) and methanol (20 mL) were stirred for 0.5 hour at the room temperature. Thereafter, ethyl acetate (20 mL) was added to dilute the mixture. The resultant mixture was washed with water and saturated brine sequentially, dried over anhydrous sodium sulfate, and filtered. The filtrate was concentrated to give a black oil b (2.4 g).

Step 3: Synthesis of 2-azido-1-methyl-4-nitrobenzene c 2-methyl-5-nitro aniline (5 g, 1 eq) was dissolved in HCl (6.0 mol/L, 4.8 eq). An aqueous solution of NaNO₂ (2.3 g, 1 eq), and then an aqueous solution of NaN₃ (2.6 g, 1.2 eq)

were added dropwise at 0° C. The mixture was stirred for 2 hours at the room temperature. Thereafter, water (200 mL) was added. The resultant mixture was filtered. The filter cake was washed with water, and dried to give a yellow solid c (5.3 g).

Step 4: Synthesis of 1-methyl-4-(5-(1-(2-methyl-5-nitrophenyl)-1H-1,2,3-triazol-4-yl)pyridin-3-yl)piperazine d 1-(5-ethynylpyridin-3-yl)-4-methylpiperazine b (2 g, 1 eq), 2-azido-1-methyl-4-nitrobenzene c (1.8 g, 1 eq), sodium ascorbate (0.4 g, 0.2 eq), CuSO$_4$ (0.16 g, 0.1 eq) and tert-butanol/water (1:1, 30 mL) were stirred overnight at 90° C. The resultant mixture was cooled, and concentrated. The concentrate was subjected to column chromatography to give a yellow solid d (3.1 g).

The synthesis of Compound 18 was completed by employing steps similar to the last two steps described in Example 1. Exact Mass (calculated): 522.21; MS (ESI) m/z (M+1)+: 523.21.

Example 19

N-(4-methyl-3-(4-(5-(4-methylpiperazin-1-yl)pyridin-3-yl)-1H-1,2,3-triazol-1-yl)phenyl)-2-(trifluoromethyl)isonicotinamide 19

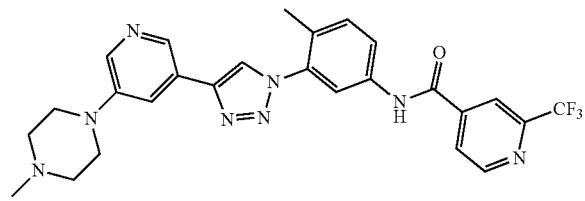 [SMILES: Cc1ccc(NC(=O)c2ccnc(C(F)(F)F)c2)cc1-n1cc(-c2cncc(N3CCN(C)CC3)c2)nn1]

Compound 19 was synthesized by employing steps similar to those described in Example 18. Exact Mass (calculated): 522.21; MS (ESI) m/z (M+1)+: 523.21.

Example 20

N-(4-methyl-3-(4-(5-(4-methylpiperazin-1-yl)pyridin-3-yl)-1H-1,2,3-triazol-1-yl)phenyl)-5-(trifluoromethyl)nicotinamide 20

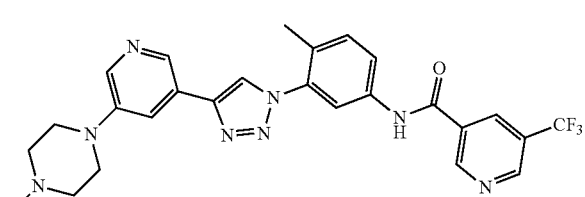

Compound 20 was synthesized by employing steps similar to those described in Example 18. Exact Mass (calculated): 522.21; MS (ESI) m/z (M+1)+: 523.21.

Example 21

N-(4-methyl-3-(4-(5-(4-methylpiperazin-1-yl)pyridin-3-yl)-1H-1,2,3-triazol-1-yl)phenyl)-4-(trifluoromethyl)picolinamide 21

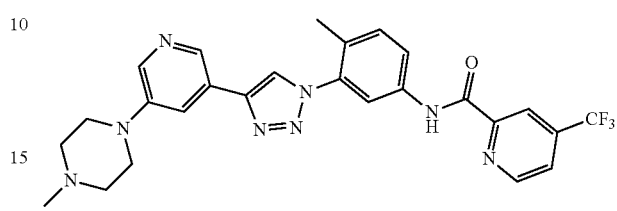

Compound 21 was synthesized by employing steps similar to those described in Example 18. Exact Mass (calculated): 522.21; MS (ESI) m/z (M+1)+: 523.21.

Example 22

6-chloro-N-(4-methyl-3-(4-(5-(4-methylpiperazin-1-yl)pyridin-3-yl)-1H-1,2,3-triazol-1-yl)phenyl)picolinamide 22

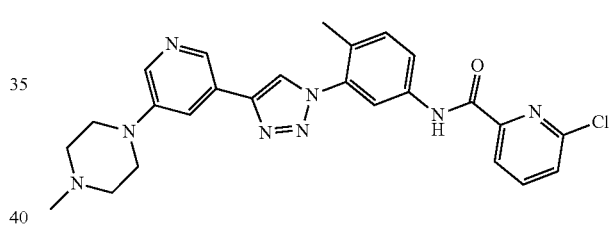

Compound 22 was synthesized by employing steps similar to those described in Example 18. Exact Mass (calculated): 488.18; MS (ESI) m/z (M+1)+: 489.18.

Example 23

6-fluoro-N-(4-methyl-3-(4-(5-(4-methylpiperazin-1-yl)pyridin-3-yl)-1H-1,2,3-triazol-1-yl)phenyl)picolinamide 23

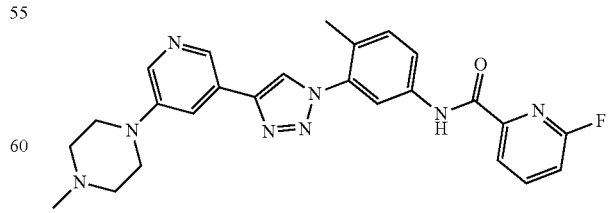

Compound 23 was synthesized by employing steps similar to those described in Example 18. Exact Mass (calculated): 472.21; MS (ESI) m/z (M+1)+: 473.21.

Example 24

N-(4-fluoro-3-(4-(5-(4-methylpiperazin-1-yl)pyridin-3-yl)-1H-1,2,3-triazol-1-yl)phenyl)-6-(trifluoromethyl)picolinamide 24

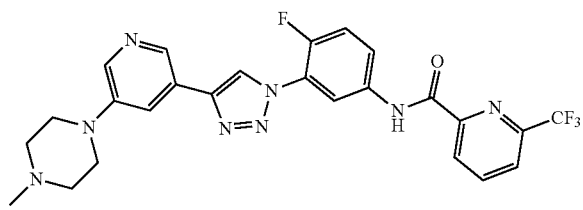 [SMILES: CN1CCN(c2cncc(-c3cn(-c4cc(NC(=O)c5cccc(C(F)(F)F)n5)ccc4F)nn3)c2)CC1]

Compound 24 was synthesized by employing steps similar to those described in Example 18. Exact Mass (calculated): 526.18; MS (ESI) m/z (M+1)+: 527.18.

Example 25

N-(4-fluoro-3-(4-(5-(4-methylpiperazin-1-yl)pyridin-3-yl)-1H-1,2,3-triazol-1-yl)phenyl)-2-(trifluoromethyl) isonicotinamide 25

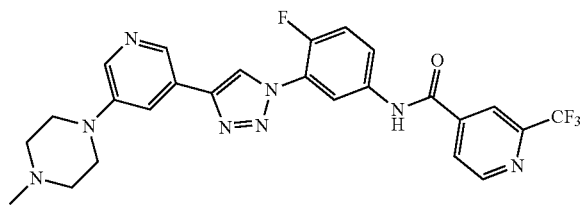 [SMILES: CN1CCN(c2cncc(-c3cn(-c4cc(NC(=O)c5ccnc(C(F)(F)F)c5)ccc4F)nn3)c2)CC1]

Compound 25 was synthesized by employing steps similar to those described in Example 18. Exact Mass (calculated): 526.18; MS (ESI) m/z (M+1)+: 527.18.

Example 26

N-(4-fluoro-3-(4-(5-(4-methylpiperazin-1-yl)pyridin-3-yl)-1H-1,2,3-triazol-1-yl)phenyl)-5-(trifluoromethyl)nicotinamide 26

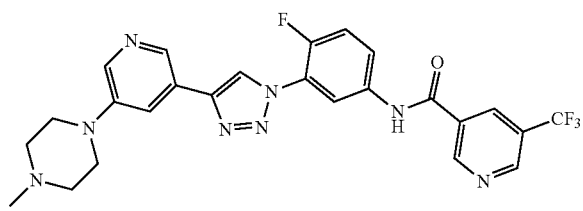 [SMILES: CN1CCN(c2cncc(-c3cn(-c4cc(NC(=O)c5cncc(C(F)(F)F)c5)ccc4F)nn3)c2)CC1]

Compound 26 was synthesized by employing steps similar to those described in Example 18. Exact Mass (calculated): 526.18; MS (ESI) m/z (M+1)+: 527.18.

Example 27

N-(4-fluoro-3-(4-(5-(4-methylpiperazin-1-yl)pyridin-3-yl)-1H-1,2,3-triazol-1-yl)phenyl)-4-(trifluoromethyl)picolinamide 27

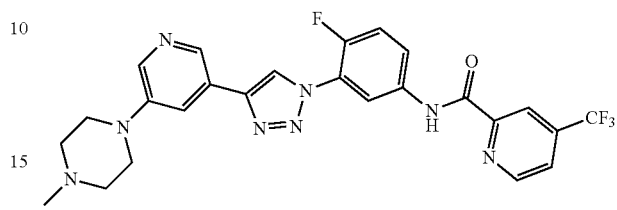

Compound 27 was synthesized by employing steps similar to those described in Example 18. Exact Mass (calculated): 526.18; MS (ESI) m/z (M+1)+: 527.18.

Example 28

6-chloro-N-(4-fluoro-3-(4-(5-(4-methylpiperazin-1-yl)pyridin-3-yl)-1H-1,2,3-triazol-1-yl)phenyl)picolinamide 28

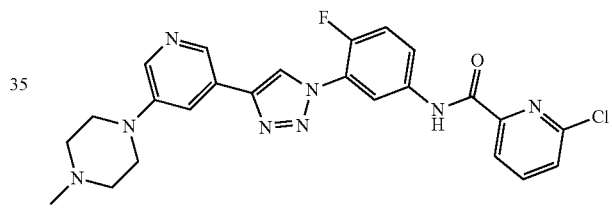

Compound 28 was synthesized by employing steps similar to those described in Example 18. Exact Mass (calculated): 492.15; MS (ESI) m/z (M+1)+: 493.15.

Example 29

6-fluoro-N-(4-fluoro-3-(4-(5-(4-methylpiperazin-1-yl)pyridin-3-yl)-1H-1,2,3-triazol-1-yl)phenyl)picolinamide 29

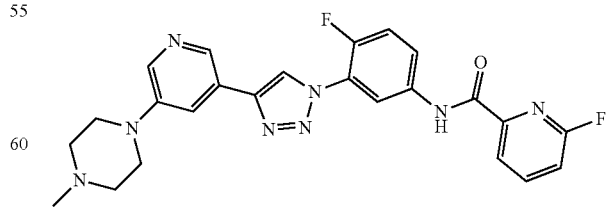

Compound 29 was synthesized by employing steps similar to those described in Example 18. Exact Mass (calculated): 476.18; MS (ESI) m/z (M+1)+: 477.18.

Example 30

6-chloro-N-(4-chloro-3-(4-(5-(4-methylpiperazin-1-yl)pyridin-3-yl)-1H-1,2,3-triazol-1-yl)phenyl)picolinamide 30

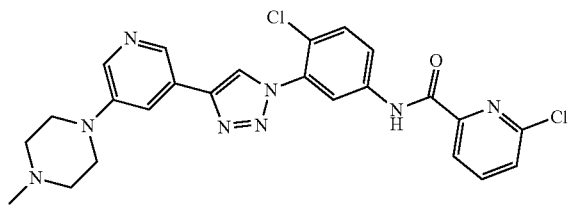 [SMILES: CN1CCN(c2cncc(-c3cn(-c4cc(NC(=O)c5cccc(Cl)n5)ccc4Cl)nn3)c2)CC1]

Compound 30 was synthesized by employing steps similar to those described in Example 18. Exact Mass (calculated): 508.12; MS (ESI) m/z (M+1)+: 509.12.

Example 31

6-fluoro-N-(4-chloro-3-(4-(5-(4-methylpiperazin-1-yl)pyridin-3-yl)-1H-1,2,3-triazol-1-yl)phenyl)picolinamide 31

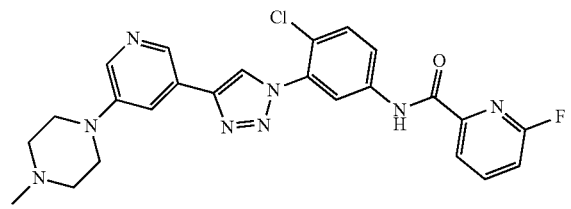 [SMILES: CN1CCN(c2cncc(-c3cn(-c4cc(NC(=O)c5cccc(F)n5)ccc4Cl)nn3)c2)CC1]

Compound 31 was synthesized by employing steps similar to those described in Example 18. Exact Mass (calculated): 492.15; MS (ESI) m/z (M+1)+: 493.15.

Example 32

N-(3-(4-(5-(2-oxa-6-aza-spiro[3.3]hept-6-yl]pyridin-3-yl)-1H-pyrazol-1-yl)-4-methylphenyl)-6-(trifluoromethyl)picolinamide 32

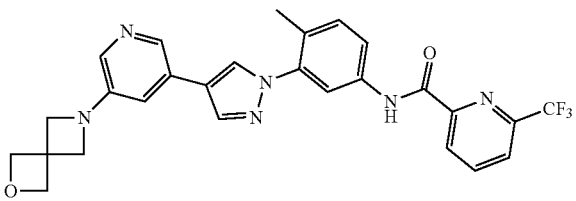 [SMILES: Cc1ccc(NC(=O)c2cccc(C(F)(F)F)n2)cc1-n1cc(-c2cncc(N3CC4(COC4)C3)c2)cn1]

Compound 32 was synthesized by employing steps similar to those described in Example 1. Exact Mass (calculated): 520.18; MS (ESI) m/z (M+1)+: 521.18.

Example 33

N-(3-(4-(5-(2-oxa-6-aza-spiro[3.3]hept-6-yl]pyridin-3-yl)-1H-pyrazol-1-yl)-4-methylphenyl)-2-(trifluoromethyl)isonicotinamide 33

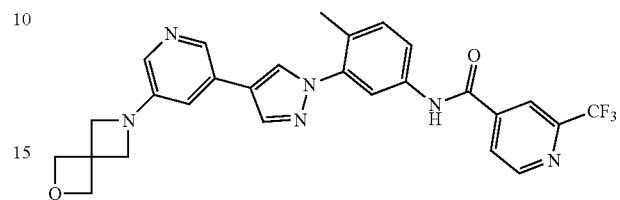

Compound 33 was synthesized by employing steps similar to those described in Example 1. Exact Mass (calculated): 520.18; MS (ESI) m/z (M+1)+: 521.18.

Example 34

N-(3-(4-(5-(2-oxa-6-aza-spiro[3.3]hept-6-yl]pyridin-3-yl)-1H-pyrazol-1-yl)-4-methylphenyl)-5-(trifluoromethyl)nicotinamide 34

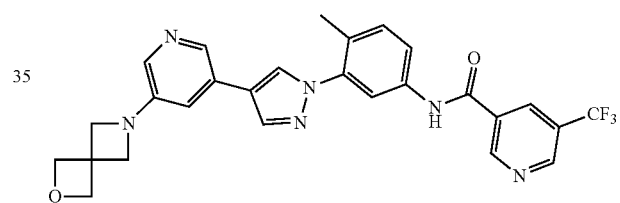

Compound 34 was synthesized by employing steps similar to those described in Example 1. Exact Mass (calculated): 520.18; MS (ESI) m/z (M+1)+: 521.18.

Example 35

N-(3-(4-(5-(2-oxa-6-aza-spiro[3.3]hept-6-yl]pyridin-3-yl)-1H-pyrazol-1-yl)-4-methylphenyl)-4-(trifluoromethyl)picolinamide 35

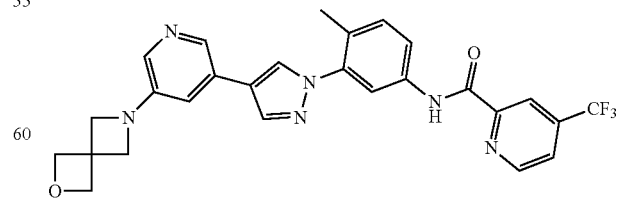

Compound 35 was synthesized by employing steps similar to those described in Example 1. Exact Mass (calculated): 520.18; MS (ESI) m/z (M+1)+: 521.18.

Example 36

N-(3-(4-(5-(2-oxa-6-aza-spiro[3.3]hept-6-yl]pyridin-3-yl)-1H-pyrazol-1-yl)-4-methylphenyl)-6-chloropicolinamide 36

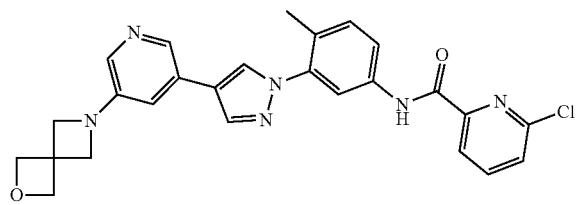 [SMILES: Cc1ccc(NC(=O)c2cccc(Cl)n2)cc1-n1cc(-c2cncc(N3CC4(COC4)C3)c2)cn1]

Compound 36 was synthesized by employing steps similar to those described in Example 1. Exact Mass (calculated): 486.15; MS (ESI) m/z (M+1)+: 487.15.

Example 37

N-(3-(4-(5-(2-oxa-6-aza-spiro[3.3]hept-6-yl]pyridin-3-yl)-1H-pyrazol-1-yl)-4-methylphenyl)-6-fluoropicolinamide 37

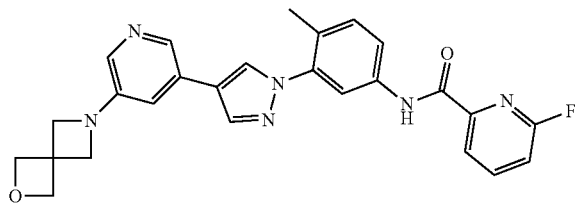 [SMILES: Cc1ccc(NC(=O)c2cccc(F)n2)cc1-n1cc(-c2cncc(N3CC4(COC4)C3)c2)cn1]

Compound 37 was synthesized by employing steps similar to those described in Example 1. Exact Mass (calculated): 470.18; MS (ESI) m/z (M+1)+: 471.18.

Example 38

N-(3-(4-(5-(2-oxa-6-aza-spiro[3.3]hept-6-yl]pyridin-3-yl)-1H-1,2,3-triazol-1-yl)-4-methylphenyl)-6-(trifluoromethyl)picolinamide 38

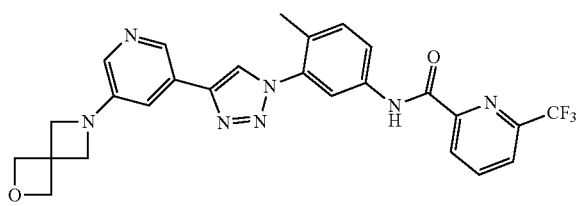 [SMILES: Cc1ccc(NC(=O)c2cccc(C(F)(F)F)n2)cc1-n1cc(-c2cncc(N3CC4(COC4)C3)c2)nn1]

Compound 38 was synthesized by employing steps similar to those described in Example 18. Exact Mass (calculated): 521.17; MS (ESI) m/z (M+1)+: 522.17.

Example 39

N-(3-(4-(5-(2-oxa-6-aza-spiro[3.3]hept-6-yl]pyridin-3-yl)-1H-1,2,3-triazol-1-yl)-4-methylphenyl)-2-(trifluoromethyl)isonicotinamide 39

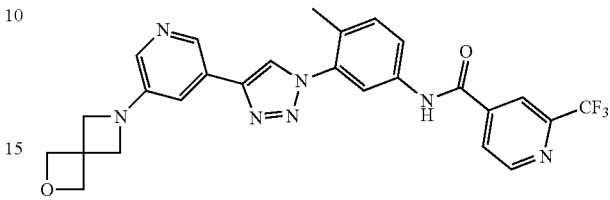

Compound 39 was synthesized by employing steps similar to those described in Example 18. Exact Mass (calculated): 521.17; MS (ESI) m/z (M+1)+: 522.17.

Example 40

N-(3-(4-(5-(2-oxa-6-aza-spiro[3.3]hept-6-yl]pyridin-3-yl)-1H-1,2,3-triazol-1-yl)-4-methylphenyl)-5-(trifluoromethyl)nicotinamide 40

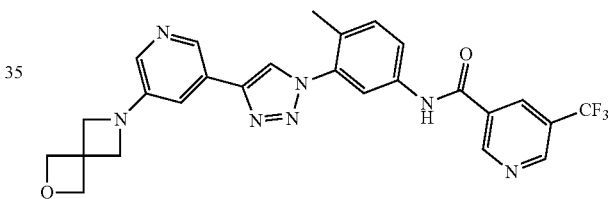

Compound 40 was synthesized by employing steps similar to those described in Example 18. Exact Mass (calculated): 521.17; MS (ESI) m/z (M+1)+: 522.17.

Example 41

N-(3-(4-(5-(2-oxa-6-aza-spiro[3.3]hept-6-yl]pyridin-3-yl)-1H-1,2,3-triazol-1-yl)-4-methylphenyl)-4-(trifluoromethyl)picolinamide 41

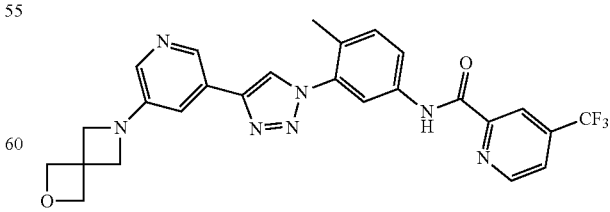

Compound 41 was synthesized by employing steps similar to those described in Example 18. Exact Mass (calculated): 521.17; MS (ESI) m/z (M+1)+: 522.17.

Example 42

N-(3-(4-(5-(2-oxa-6-aza-spiro[3.3]hept-6-yl)pyridin-3-yl)-1H-1,2,3-triazol-1-yl)-4-methylphenyl)-4-chloropicolinamide 42

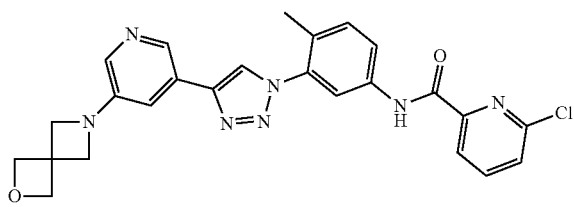 [SMILES: Cc1ccc(NC(=O)c2cccc(Cl)n2)cc1-n1cc(-c2cncc(N3CC4(COC4)C3)c2)nn1]

Compound 42 was synthesized by employing steps similar to those described in Example 18. Exact Mass (calculated): 487.15; MS (ESI) m/z (M+1)+: 488.15.

Example 43

N-(3-(4-(5-(2-oxa-6-aza-spiro[3.3]hept-6-yl)pyridin-3-yl)-1H-1,2,3-triazol-1-yl)-4-methylphenyl)-4-fluoropicolinamide 43

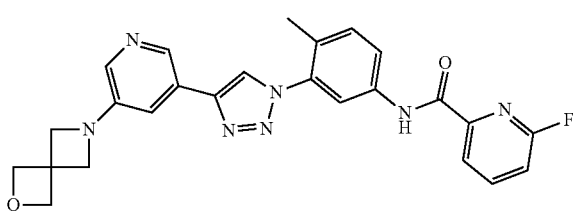 [SMILES: Cc1ccc(NC(=O)c2cccc(F)n2)cc1-n1cc(-c2cncc(N3CC4(COC4)C3)c2)nn1]

Compound 43 was synthesized by employing steps similar to those described in Example 18. Exact Mass (calculated): 471.18; MS (ESI) m/z (M+1)+: 472.18.

Example 44: Effect of the Novel Kinase Inhibitor on Growth of Cancer Cells

In this example, mouse primary B cell BaF3 (purchased from ATCC, U.S.A.) was used. In addition, in this example, mouse BaF3-tel-PDGFRα (stably expressing PDGFRα kinase), mouse BaF3-tel-PDGFRβ (stably expressing PDGFRβ kinase), BaF3-P210 (stably expressing ABL kinase), BaF3-P210-T315I (stably expressing ABL-T315I kinase), BaF3-FL-BRAF-V600E (stably expressing BRAF-V600E kinase), BaF3-TEL-cKIT (stably expressing cKIT kinase), BaF3-TEL-VEGFR2 (stably expressing VEGFR2 kinase), BaF3-TEL-FGFR2 (stably expressing FGFR2 kinase) were also used. The above-mentioned cell trains were all constructed in our laboratory by the method as follows. The sequences of human BCR-ABL (P210 or P210/T315I mutated), full-length BRAF-V600E, cKIT, VEGFR2, FGFR2, PDGFRα, PDGFRβ kinase region were amplified respectively via PCR, and inserted respectively into a MSCV-Puro vector (purchased from Clontech) having a N-terminal TEL fragment and/or NPM fragment and/or TPR fragment, and stably transferred into mouse BaF3 cells by the retroviral method, and the growth factor IL-3 was removed. Eventually, cell lines which are transferred into proteins depending on PDGFRα, PDGFRβ were obtained.

In this example, solutions of the test compound at different concentrations (0.000508 μM, 0.00152 μM, 0.00457 μM, 0.0137 μM, 0.0411 μM, 0.123 μM, 0.370 μM, 1.11 μM, 3.33 μM, 10 μM) were added to the above cells. The cells were incubated for 72 hours. The incubated cells were detected by a Cell Titer-Glo Cell Viability Assay Kit (purchased from Promega, U.S.A.) (by use of the Cell Tier-Glo, the cell viability is calculated by measuring the luminescence value, which is in proportion to the amount of ATP that is positively associated with the number of vial cells, hence, the cell viability may be obtained by detecting the amount of ATP), to quantify the number of viable cells with a microplate reader. The median inhibitory concentration $GI_{50}$ of respective compounds and control compounds against proliferation of respective cell lines were calculated (with the results as shown in Tables 1 and 2). The results indicate that the tested compounds have a very strong inhibitory effect against each of PDGFRα and PDGFRβ, and Compound 1 has no inhibitory effect, or a relatively weak inhibitory effect, against other kinase targets, such as, BRAF-V600E, ABL, ABL-T315I, cKIT, VEGFR2, FGFR2.

TABLE 1

| $GI_{50}(\mu M)$ | BaF3 | BaF3-tel-PDGFRβ | BaF3-tel-PDGFRα |
|---|---|---|---|
| Compound 1 | 4.081 | 0.43 | 0.056 |
| Compound 2 | 9.294 | 0.04 | 0.0028 |
| Compound 3 | 6.5 | 0.0014 | 0.0014 |
| Compound 4 | ~10 | 0.0032 | <0.0003 |
| Compound 5 | ~10 | <0.0003 | <0.0003 |
| Compound 6 | >10 | 0.001 | <0.0003 |
| Compound 7 | >10 | 0,001 | <0.0003 |
| Compound 8 | >10 | 0.0013 | |
| Compound 9 | >10 | <0.0003 | |
| Compound 10 | >10 | 0.062 | |
| Compound 11 | >10 | 0.0011 | |
| Compound 12 | ~10 | 0.001 | |
| Compound 13 | >10 | 0.0055 | 0.0016 |
| Compound 14 | 8.4 | <0.0015 | <0.0015 |
| Compound 15 | 3.9 | <0.0015 | <0.0015 |
| Compound 16 | >10 | <0.0015 | <0.0015 |
| Compound 17 | 2.8 | <0.0015 | <0.0015 |
| Compound 19 | >10 | <0.01 | <0.01 |
| Compound 20 | 5.07 | <0.01 | <0.01 |
| Compound 21 | 2.84 | <0.01 | <0.01 |
| Compound 22 | 0.96 | <0.01 | <0.01 |
| Compound 24 | 4.76 | <0.01 | <0.01 |
| Compound 25 | 5.55 | <0.01 | <0.01 |
| Compound 26 | 4.74 | <0.01 | <0.01 |
| Compound 27 | 4.73 | <0.01 | <0.01 |
| Compound 28 | 3.9 | <0.01 | <0.01 |
| Compound 29 | 2.84 | <0.01 | <0.01 |
| Compound 32 | 9.2 | <0.01 | <0.01 |
| Compound 33 | 6.49 | <0.01 | <0.01 |
| Compound 34 | >10 | <0.01 | <0.01 |
| Compound 35 | 5.84 | <0.01 | <0.01 |
| Compound 36 | 9.76 | <0.01 | <0.01 |
| Compound 37 | 9.85 | <0.01 | <0.01 |
| Compound 38 | >10 | <0.01 | <0.01 |
| Compound 39 | >10 | <0.01 | <0.01 |
| Compound 40 | 9.99 | <0.01 | <0.01 |
| Compound 41 | 3.66 | <0.01 | <0.01 |
| Compound 42 | >10 | <0.01 | <0.01 |
| Compound 43 | >10 | <0.01 | <0.01 |

TABLE 2

| $GI_{50}(\mu M)$ | Compound 1 |
|---|---|
| BaF3 | 4.081 |
| BaF3-P210 | >10 |
| BaF3-P210-T315I | 5.159 |
| BaF3-FL-BRAF-V600E | 4.7 |

TABLE 2-continued

| GI$_{50}$(μM) | Compound 1 |
| --- | --- |
| BaF3-TEL-cKIT | 5.343 |
| BaF3-TEL-PDGFRβ | 0.43 |
| BaF3-TEL-PDGFRα | 0.056 |
| BaF3-TEL-VEGFR2 | 4 |
| BaF3-TEL-FGFR2 | 3.256 |

Example 45: Experimental Results of Compound 1 in Mouse Models of Human Chronic Eosinophilic Leukemia Cell EOL-1 (Expressing PDGFRα)

1) Bal b/c female mice, 4-6 weeks old, were purchased from Shanghai SLAC Laboratory Animal Co., Ltd., and were raised in an SPF laboratory; the drinking water and the bedding were both sterilized by autoclaving; and all the operations involving the mice were performed under aseptic conditions;
2) On Day 0, 1×10$^7$ human chronic eosinophilic leukemia cells EOL-1 (expressing PDGFRα) (purchased from ATCC) were injected subcutaneously into the left flank of each of the mice;
3) On Day 15, the mice were randomly divided into four groups with five mice per group, and were administered respectively for 14 days. The mice in Group 1 were intraperitoneally administered with methylcellulose vehicle (purchased from Sangon); the mice in Groups 2 and 3 were administered with Compound 1 at a dose of 1 mg/kg mouse weight and 5 mg/kg mouse weight, respectively; the mice in Group 4 were administered with imatinib at a dose of 25 mg/kg (purchased from MCE, Shanghai);
4) From Day 15, the length/width of the subcutaneous tumors was measured daily with a vernier caliper, and the body weight of the mice was recorded daily to determine the effect of Compound 1 on the body weight of the mice;
5) On Day 29, the mice were sacrificed with carbon dioxide, and the subcutaneous tumors were removed and weighed for comparison;
6) The growth trend of the subcutaneous tumor within 15-29 days was statistically analyzed. The tumor volume was calculated as length×width×width/2 mm$^3$.

Figure 1B:
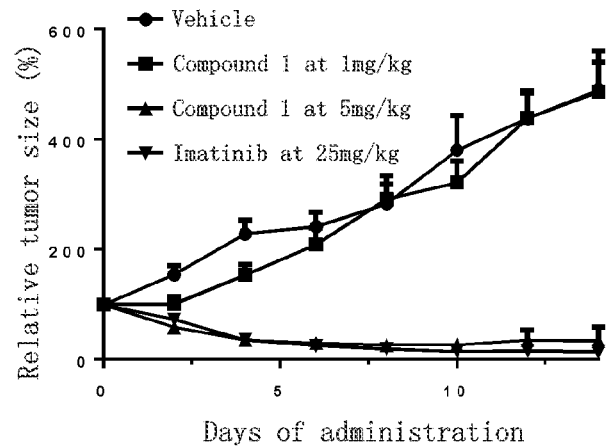
FIG. 1b shows the change in the mean size of tumors over time in different treatment groups using Compound 1, imatinib and vehicle in a mouse tumor model of human chronic eosinophilic leukemia cells EOL-1.
Figure 1C:
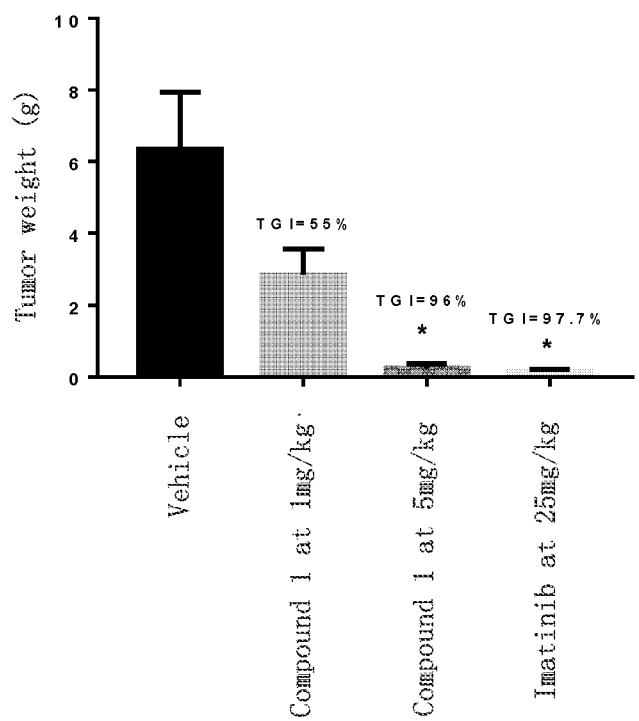
FIG. 1c shows the average weight of tumors and the calculated tumor inhibitory rate of mice on Day 14 after administration in different treatment groups using Compound 1, imatinib and vehicle in a mouse tumor model of human chronic eosinophilic leukemia cells EOL-1.

The results were shown in FIGS. 1a-1c. FIG. 1a showed the change in the mean body weight of mice over time in different treatment groups (shown in the figure as a relative body weight: the percentage calculated based on the mouse weight at the beginning of the administration) in the mouse tumor model of human chronic eosinophilic leukemia cell EOL-1; FIG. 1b showed the change in the mean size of tumors over time in different treatment groups (shown in the figure as a relative tumor size: percentage calculated based on the size of the tumor beared in the mouse at the beginning of the administration) in the mouse tumor model of human chronic eosinophilic leukemia cell EOL-1; FIG. 1c showed the mean tumor weight and the calculated tumor growth inhibitory rate of the mice in different treatment groups 14 days after administration in the mouse tumor model of human chronic eosinophilic leukemia cell EOL-1.

The experimental results of FIG. 1b showed that the group administered with Compound 1 at a dose of 5 mg/kg exhibited an excellent effect in inhibiting the tumor in the mouse in the mouse tumor model of human chronic eosinophilic leukemia cell EOL-1 (expressing PDGFRα). The experimental results of FIG. 1c showed that the tumor growth inhibitory rate was as high as 96% 14 days after administration in the mouse model of human chronic eosinophilic leukemia cell EOL-1 for the group administered with Compound 1 at a dose of 5 mg/kg (see FIG. 1c), wherein the tumor growth inhibitory rate (TGI)=(weight of the tumor in the control group-weight of the tumor in the test group)/weight of the tumor in the control group. This indicated that Compound 1 of the present invention can significantly inhibit the tumor growth in the animal model of human chronic eosinophilic leukemia cell EOL-1 (expressing PDGFRα). Moreover, the results of FIG. 1a also showed that Compound 1 not only effectively inhibited the tumor growth in the mouse, but also had little effect on the body weight of the mouse, suggesting that Compound 1 is suitable for administering to an animal.

Example 46: Experimental Results of Compound 1 in a Rat Model of Pulmonary Arterial Hypertension (PAH)

120 male SD rats weighed 180+20 g were provided by Qinglongshan Animal Breeding Center with a License No. SCXK (SU) 2017-0001. These rats were fed with conventional pellet feeds (Jiangsu Xietong Bio. Co., Ltd.), and were raised in a clean animal room with 12h/12h light/dark cycle. The rats were fed with foods and drinking water on an ad libitum basis. The temperature was maintained at 20-26° C., and the relative humidity was 40-70%.

120 SD rats were divided into 24 cages with 5 rats per group. After an adaptive growth for 7 days without any abnormal conditions, 110 rats were induced to construct a pulmonary arterial hypertension model, and the remaining 10 rats were used for normal control. The animals were treated in strict accordance with animal ethics regulations throughout the experiment.

According to the method described in "Pharmaceutical experimental animal models: Fabrication and application" and the Standard Operating Procedure for PAH Model Construction of Model Animal Center, rats were intraperitoneally injected with a solution of 1% monocrotaline (MCT, purchased from Sigma, U.S.A.) once at a dose of 35 mg/kg. On Day 7 after the first injection of MCT, MCT was injected again at a dose of 20 mg/kg. The rats in the normal control group were intraperitoneally injected with an equivalent amount of water as a blank solvent. The specific steps were as follows:

After the rats in each of the cages were fasted for 8 hours, each of the rats was weighed and recorded for the basic body weight after fasting; based on the measured basic body weight for each of the rats, the amount of MCT required to be injected for each of the rats was calculated according to the modeling dose of 35 mg/kg; based on the amount of MCT required to be injected for each of the rats, the dose for injection of a 1% MCT solution was calculated; the rats were fixed in a holder and intraperitoneally injected with the 1% MCT solution at the calculated dose; the rats were returned to the cages for routine feeding after the injection.

The tail artery blood was taken for the blood gas analysis at Week 3 and Week 4, respectively, after the injection of MCT. 0.5 mL of tail artery blood was drawn slowly, transferred into an anticoagulation tube, and loaded in a blood gas analyzer to determine the indexes of partial pressure of oxygen (pO$_2$), partial pressure of carbon dioxide (pCO$_2$) and blood oxygen saturation (SaO$_2$) in the blood. The blood gas analyzer was operated following the standard operation procedure. Based on the measured results, the rats with pulmonary hypertension were randomly divided into the following groups (10 rats per group): a negative control group (i.e., a vehicle group), a group of 50 mg/kg bosentan, a drug for clinically treating pulmonary hypertension (purchased from MCE, Shanghai), a group of 50 mg/kg imatinib, a group of 45 mg/kg Compound 1, a group of 30 mg/kg Compound 1, and a group of 15 mg/kg Compound 1. Each of the rats was administered by gavage once a day starting from the day of regrouping at Week 4. The rats in the negative control group were daily administered by gavage with an equal volume of methylcellulose as vehicle. The rats in each of the groups were administered by gavage for consecutive 4 weeks (i.e., 28 days). For each of the rats in respective groups, the condition, the occurrence of symptoms of dyspnea, decreased activity, accelerated heartbeat and the like, was observed at the same time of daily gavage. The rats were weighed after fasting overnight twice a week. The administration dosage was calculated based on the weighing results.

Determination of the pulmonary arterial pressure and the right ventricular systolic pressure of rats: at the end of the experiment (28 days after administration by gavage), the rats were weighed, and anesthetized by intraperitoneal injection of 10% chloral hydrate (purchased from Sangon) (0.3 mL/100 g). After the rats were under anesthesia, the pulmonary arterial pressure and the right ventricular systolic pressure of rats were measured. The measurement method may be found in the standard operating procedures of the function experimental system. The steps were as follows.

A No. 3.5 umbilical vein catheter was connected to a system pressure transducer. A formulated solution of heprin sodium (purchased from Sangon) was filled into the transducer and the catheter, and bubbles were discharged. The anesthetized rat was placed on a surgical anatomical plate that is adjustable in its temperature. The temperature of the plate was adjusted to be maintained at about 37° C. The rat was fixed in supine position. The neck skin was cut with scissors to the edge of the clavicle, followed by blunt dissection of subcutaneous tissues and muscles, exposing the right external jugular vein. The adipose tissue on the surface was removed with ophthalmic surgical scissors. The external jugular vein was ligated at the telecentric end with surgical thread, and a loose knot was made at the proximal end for reserve. The external jugular vein was gently lifted with ophthalmic tweezers and cut with ophthalmic scissors to make a "V" opening. The catheter was quickly inserted, and the loose knot at the proximal end was tightened slightly to prevent bleeding. The bending of the catheter in the anterior segment was kept towards the left, and at about 1-1.5 cm, the catheter was further inserted to the position of 2 cm while keeping away the axillary vein of the rat, to approach the right auricle. At this time, the catheter was gently rotated clockwise for 100-180° C. while keeping away the right auricle. At about 3 cm, the end of the catheter entered into the right atrium, and was further inserted to reach the atrioventricular orifice at about 4-4.5 cm. At this time, the catheter was gently rotated counterclockwise for 90-180° to hook the atrioventricular orifice and enter the right ventricle, and meanwhile a right ventricular wave with relatively large amplitude was observed. The catheter was further inserted slowly forward, and entered into the pulmonary artery at about 5 cm.

Key points of the measurement: the catheter was inserted at 1-2 cm to reach the precava, at 2-3 cm to reach the right atrium, at about 4 cm to enter into the right ventricle, and at about 5 cm to enter into the pulmonary artery. The pressure of the right atrium was close to zero, and the pressure of the pulmonary artery was the highest.

After the pulmonary artery measurement, the abdominal cavity of rats was cut open, and the abdominal aorta was carefully separated. 3 mL of blood was drawn slowly from aorta by inserting the needle directing towards the proximal end of the abdominal aorta using a 5 ml syringe infiltrated with a solution of sodium heparin. The blood was transferred into an anticoagulation tube, and loaded in a blood gas analyzer to determine the indexes of partial pressure of oxygen ($pO_2$), partial pressure of carbon dioxide ($pCO_2$) and blood oxygen saturation ($SaO_2$) in the blood.

At the end of the experiment, the rats were sacrificed, and their hearts were taken out. The right ventricle (RV) and the left ventricle and septum (LV+S) were separated, respectively, washed with physiological saline, and the moisture was absorbed by a filter paper. RV and LV+S were weighed, respectively. The right ventricular index (RVI) obtained by the following formula was used as the evaluation index of right heart hypertrophy: RVI=RV/(LV+S).

Figure 2A:
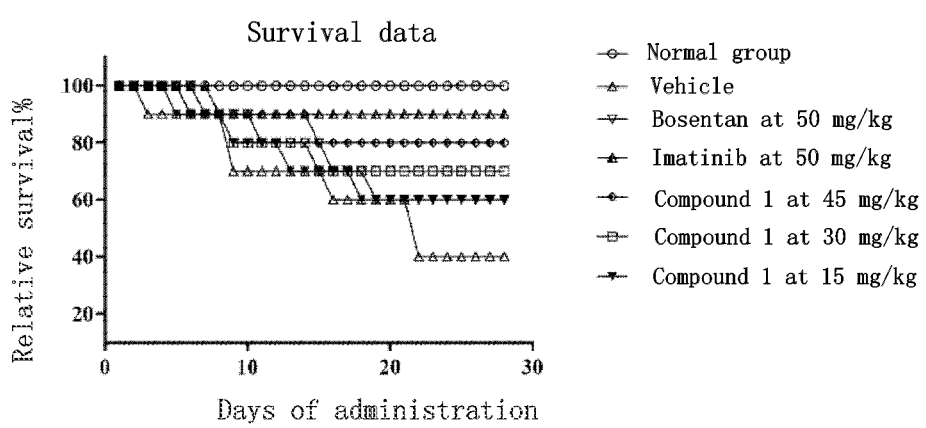
FIG. 2a shows the change in the survival rate of rats over time in different treatment groups using Compound 1, imatinib, bosentan and vehicle in a rat pulmonary hypertension model.
Figure 2B:
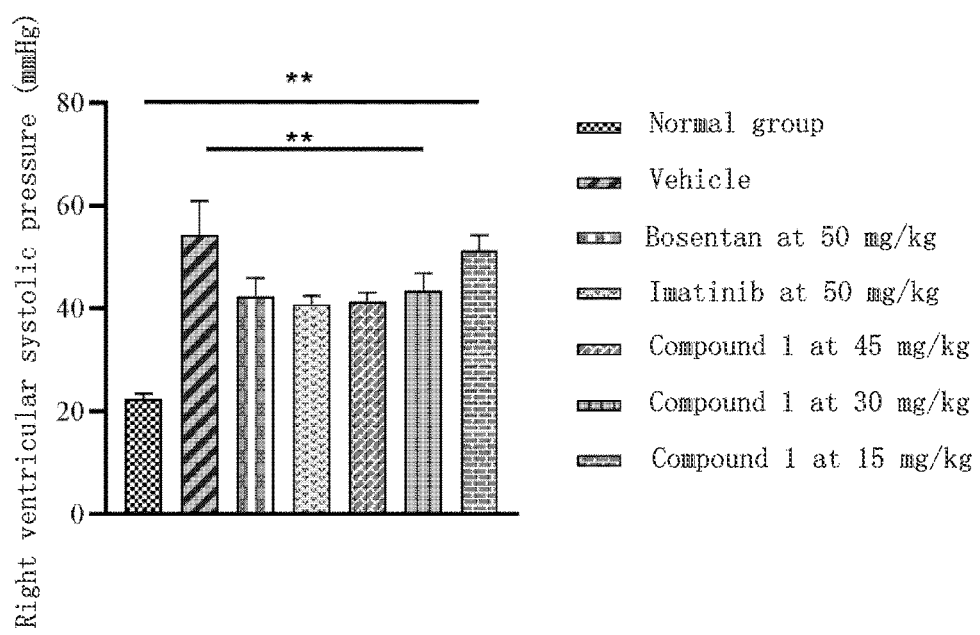
FIG. 2b shows the right ventricular systolic blood pressure of rats in different treatment groups using Compound 1, imatinib, bosentan, and vehicle in a rat pulmonary hypertension model.

The results were shown in FIGS. 2a-2b. FIG. 2a showed the change in the survival rate of rats over time in different treatment groups (shown in the figure as a relative survival rate: the percentage calculated based on the number of rats at the beginning of the experiment) in the rat pulmonary hypertension model; and FIG. 2b showed the right ventricular systolic pressure in different treatment groups in the rat pulmonary hypertension model.

As can be seen from the significant difference analysis of the mean pulmonary artery pressure (mPAP) of respective groups, as compared with the normal group, the vehicle group was extremely significantly different ($p<0.001$); the imatinib group (n=10, 27.27+2.02) with the lowest mPAP was about 1.5 times the normal group (n=10, 18.33+0.23); as compared with the vehicle group, each of the two groups of a positive drug, the group of 45 mg/kg Compound 1, the group of 30 mg/kg Compound 1, and the group of 15 mg/kg Compound 1 was extremely significantly different ($p<0.001$). The high-dose group of 45 mg/kg Compound 1 and the medium-dose group of 30 mg/kg Compound 1 showed no significant difference as compared with each of the group of bosentan and the group of imatinib, and extremely significant difference as compared with each of the other groups ($p<0.001$).

As can be seen from the significant difference analysis of the right ventricular systolic pressure (RVSP) of respective groups, as compared with the normal group, the vehicle group was extremely significantly different ($p<0.001$); the group of imatinib with the lowest RVSP (n=10, 40.84+1.49) was about 1.8 times the normal group (n=10, 22.44+1.09); each of the two groups of a positive drug, the high-dose group of 45 mg/kg Compound 1 and the medium-dose group of 30 mg/kg Compound 1 was extremely significantly different as compared with the vehicle group ($P<0.001$). The high-dose group of 45 mg/kg Compound 1 and the medium-dose group of 30 mg/kg Compound 1 showed no significant difference as compared with each of the group of imatinib and the group of bosentan, and extremely significant difference as compared with each of the other groups ($p<0.001$).

The partial pressure of oxygen ($pO_2$) in the artery, which reflects the oxygen uptake of pulmonary capillaries, is an index reflecting the respiration status, and is the most sensitive index of whether the body is hypoxic. The $pO_2$ under a normal condition is 80~110 mmHg. The $pO_2$ that is lower than 80 mmHg reflects that the body is hypoxic. The partial pressure of carbon dioxide in the arterial blood is an important index reflecting the respiratory acid-base balance condition, and is 35~45 mmHg under a normal condition. In the case of abnormal pulmonary function and insufficient ventilation, the partial pressure of $CO_2$ is increased for reasons such as the excessively low $CO_2$ emission, which is respiratory acidosis. The blood oxygen saturation $SaO_2$ which is an index reflecting the percentage of the capability of oxyhemoglobin ($HbO_2$) based on the total capability of hemoglobin (Hb) available for binding the oxygen, is an important physiological parameter of respiratory circulation. If a pathological change occurs in the lung function, hypoxia will occur, resulting in a decrease in the blood oxygen saturation. Under a normal condition, $SaO_2 \geq 90\%$.

After intervention by administration, the partial pressure of oxygen, the partial pressure of carbon dioxide and the blood oxygen saturation were changed to varying degrees in each of the groups. The data analysis of the partial pressure of oxygen showed that, as compared with the vehicle group, the groups of a positive drug and the high-dose group of Compound 1 were extremely significantly different (P<0.001), and the medium-dose group of Compound 1 was extremely significantly different (P<0.01). A comparison of the rats in each of the groups showed that the partial pressure of oxygen of the rats in part of the groups was within the range of the normal control group, indicating that the drug treatment plays a certain role in maintenance and recovery of the partial pressure of oxygen.

The data analysis of the partial pressure of carbon dioxide for respective groups showed that, as compared with the vehicle group, the groups of a positive drug and the high-dose group of Compound 1 were extremely significantly different (P<0.001), and the the medium-dose group of Compound 1 was extremely significantly different (P<0.01). A comparison of the rats in each of the groups showed that the partial pressure of carbon dioxide in part of the groups was within the range of the normal control group, indicating that the drug treatment plays a certain role in recovery of pulmonary ventilation in the rats with pulmonary hypertension.

The data analysis of the blood oxygen saturation for respective groups showed that, as compared with the vehicle group, the groups of a positive drug and the high-dose group of Compound 1 were significantly different (p<0.05). A comparison of the rats in each of the groups showed that the blood oxygen saturation of part of the groups was within the range of the normal control group.

RVI refers to an index measurement for right ventricular hypertrophy in the rat. The measured results showed that, after intervention by administration, the right ventricular hypertrophy index in each of the groups was changed to varying degrees, wherein the RVI of the group of bosentan was decreased by 15.7% as compared with that of the negative control group, and the RVI of the group of imatinib was decreased by 17.8% as compared with that of the negative control group, the RVI of the high-dose group of 45 mg/kg Compound I was decreased by 29.6% as compared with the negative control group, the RVI of the medium-dose group of 30 mg/kg Compound 1 was decreased by 9.4% as compared with the negative control group, and the RVI of the low-dose group of 15 mg/kg Compound 1 was decreased by 5.5% as compared with the negative control group.

The significant difference analysis of RVI for respective groups showed that, as compared with the normal group, the vehicle group was extremely significantly different (p<0.001); the group of imatinib with the lowest RVI (n=10, 0.403+0.016) was about 1.4 times the normal group (n=10, 0.279+0.16); each of the two groups of a positive drug and the high-dose group of 45 mg/kg Compound 1 was extremely significantly different as compared with the vehicle group (P<0.001). The high-dose group of 45 mg/kg Compound 1 showed no significant difference as compared with each of the group of imatinib and the group of bosentan, and extremely significant difference as compared with each of the other groups (p<0.001).

INDUSTRIAL APPLICABILITY

The invention provides a selective PDGFR kinase inhibitor, which is useful in inhibiting the activity of PDGFR kinase and in treating a disease, a disorder or a condition related to inhibition of the activity of PDGFR kinase. Therefore, it may be prepared into corresponding medicament and has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

The invention claimed is:
1. A PDGFR kinase inhibitor, which is a compound of formula (I) or a pharmaceutically acceptable salt, solvate, ester, acid, metabolite or prodrug thereof:

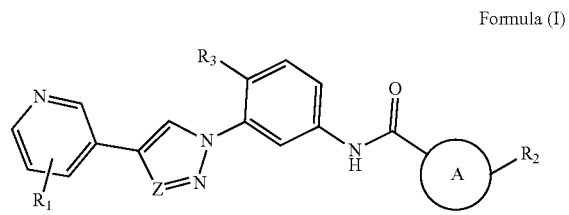

Formula (I)

wherein,
the A ring is a pyridine ring;
Z is CH;
$R_1$ is selected from the group consisting of heterocycloalkyl, heterocycloalkyloxy, heterocycloalkyl $C_{1-6}$ alkoxy, heterocycloalkylamino, heterospirocycloalkyl, heterospirocycloalkylamino, $C_{3-6}$ cycloalkyl $C_{1-6}$ alkoxy, $C_{3-6}$ cycloalkyloxy, wherein the heterocycloalkyl is a 4- to 8-membered heterocycloalkyl containing oxygen and/or nitrogen atom(s), and the nitrogen atom in the heterocycloalkyl is optionally substituted with $C_{1-6}$ alkyl;
$R_2$ is selected from the group consisting of halogen and $C_{1-6}$ haloalkyl;
$R_3$ is selected from the group consisting of $C_{1-6}$ alkyl and halogen.

2. The PDGFR kinase inhibitor according to claim 1, wherein the A ring is selected from the group consisting of

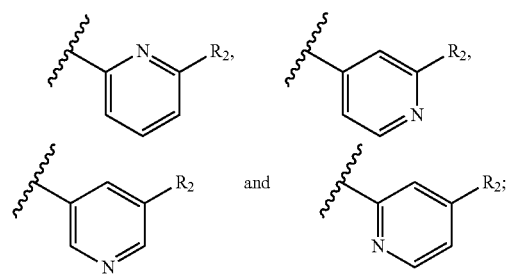

$R_2$ is selected from the group consisting of fluorine, chlorine and trifluoromethyl.

3. The PDGFR kinase inhibitor according to claim 1, wherein $R_3$ is selected from the group consisting of methyl, fluorine and chlorine.

4. The PDGFR kinase inhibitor according to claim 1, which is a compound of formula (Ia) or a pharmaceutically acceptable salt, solvate, ester, acid, metabolite or prodrug thereof:

Formula (Ia)

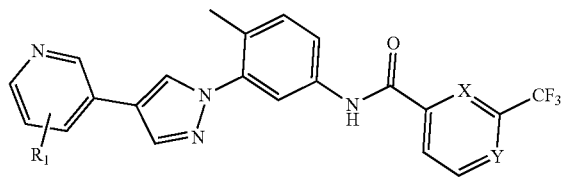

wherein,
$R_1$ is selected from the group consisting of heterocycloalkyl, heterocycloalkyloxy, heterocycloalkyl $C_{1-6}$ alkoxy, heterocycloalkylamino, heterospirocycloalkyl, heterospirocycloalkylamino, $C_{3-6}$ cycloalkyl $C_{1-6}$ alkoxy, $C_{3-6}$ cycloalkyloxy, wherein the heterocycloalkyl is a 4- to 6-membered heterocycloalkyl containing oxygen and/or nitrogen atom(s), and the nitrogen atom in the heterocycloalkyl is optionally substituted with $C_{1-6}$ alkyl; and
one of X and Y is CH and the other is N.

5. The PDGFR kinase inhibitor according to claim 1, wherein the substituent of $R_1$ is substituted on the carbon at a para- or meta-position of the N atom in the pyridine ring.

6. The PDGFR kinase inhibitor according to claim 1, wherein the heterocycloalkyl is selected from the group consisting of pyrrolidinyl, morpholinyl, piperazinyl, tetrahydropyranyl, tetrahydrofuranyl, oxetanyl and azetidinyl, and the heterospirocycloalkyl is selected from 6- to 10-membered spirocycloalkyl groups containing oxygen and/or nitrogen heteroatom(s).

7. The PDGFR kinase inhibitor according to claim 1, wherein $R_1$ is selected from the group consisting of $C_{1-6}$ alkyl piperazinyl, morpholinyl, tetrahydropyranyl $C_{1-6}$ alkoxy, oxetanyloxy, morpholino $C_{1-6}$ alkoxy, tetrahydrofuranyl $C_{1-6}$ alkoxy, $C_{3-6}$ cycloalkyl $C_{1-6}$ alkoxy and oxa-aza-spiroheptyl.

8. The PDGFR kinase inhibitor according to claim 1, wherein $R_1$ is selected from the group consisting of N-methyl piperazin-1-yl, N-morpholinyl, tetrahydropyran-4-yl methoxy, oxetan-3-yloxy, 2-morpholinoethoxy, tetrahydrofuran-2-yl methoxy, cyclopentyl methoxy and 2-oxa-6-aza-spiro[3.3]hept-6-yl.

9. The PDGFR kinase inhibitor according to claim 1, which is a compound selected from the group consisting of:

| Compound No. | Compound Structure |
|---|---|
| 1 | 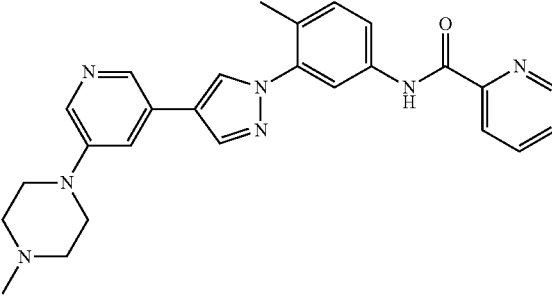 |
| 2 | 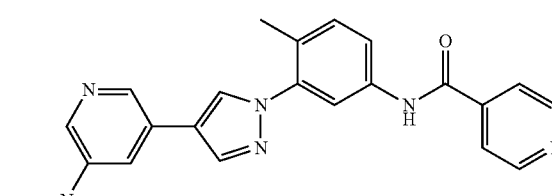 |

| Compound No. | Compound Structure |
|---|---|
| 3 | 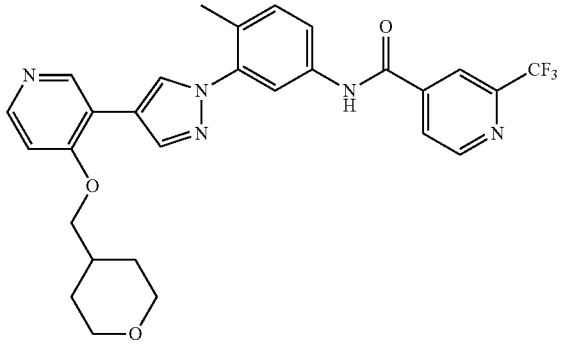 [SMILES: Cc1ccc(NC(=O)c2ccnc(C(F)(F)F)c2)cc1-n1cc(-c2cnccc2OCC2CCOCC2)cn1] |
| 4 | 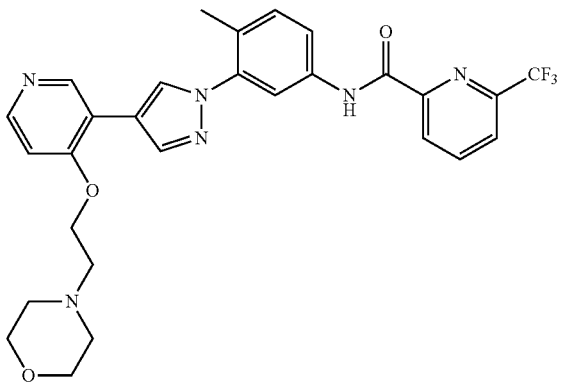 [SMILES: Cc1ccc(NC(=O)c2cccc(C(F)(F)F)n2)cc1-n1cc(-c2cnccc2OCCN2CCOCC2)cn1] |
| 5 | 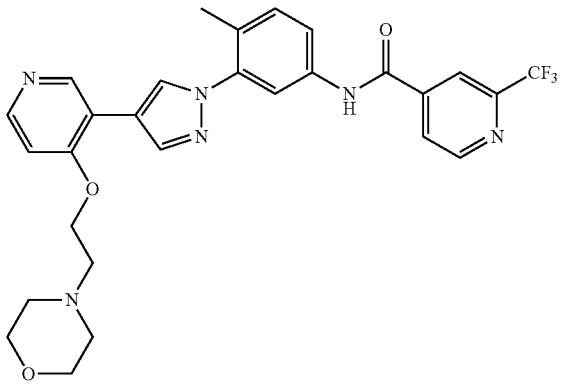 [SMILES: Cc1ccc(NC(=O)c2ccnc(C(F)(F)F)c2)cc1-n1cc(-c2cnccc2OCCN2CCOCC2)cn1] |
| 6 | 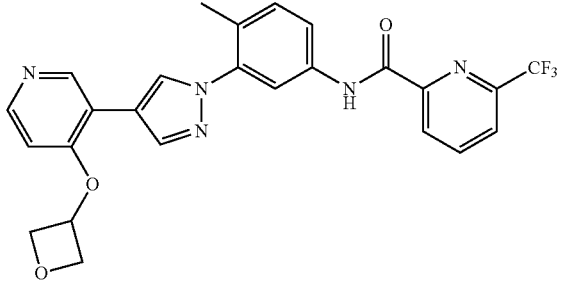 [SMILES: Cc1ccc(NC(=O)c2cccc(C(F)(F)F)n2)cc1-n1cc(-c2cnccc2OC2COC2)cn1] |

-continued

| Compound No. | Compound Structure |
|---|---|
| 7 | 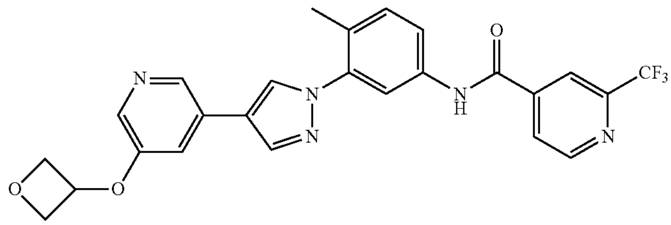 [SMILES: Cc1ccc(NC(=O)c2ccnc(C(F)(F)F)c2)cc1-n1cc(-c2cncc(OC3COC3)c2)cn1] |
| 8 | 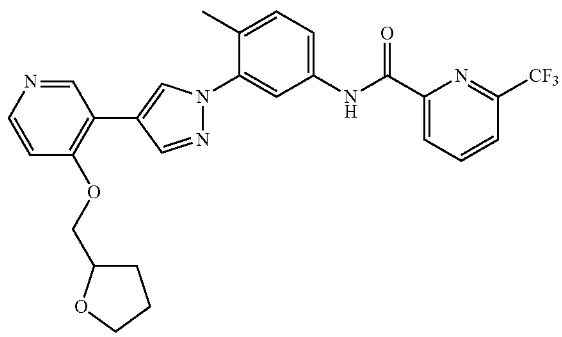 [SMILES: Cc1ccc(NC(=O)c2cccc(C(F)(F)F)n2)cc1-n1cc(-c2cnccc2OCC2CCCO2)cn1] |
| 9 | 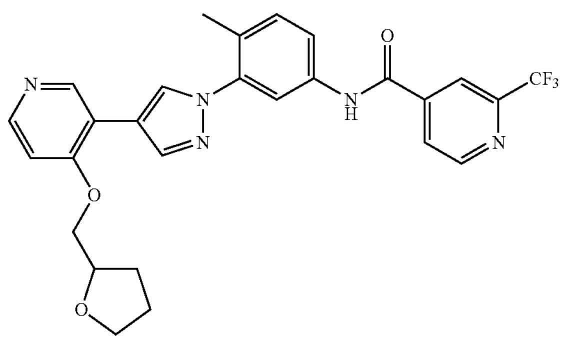 [SMILES: Cc1ccc(NC(=O)c2ccnc(C(F)(F)F)c2)cc1-n1cc(-c2cnccc2OCC2CCCO2)cn1] |
| 10 | 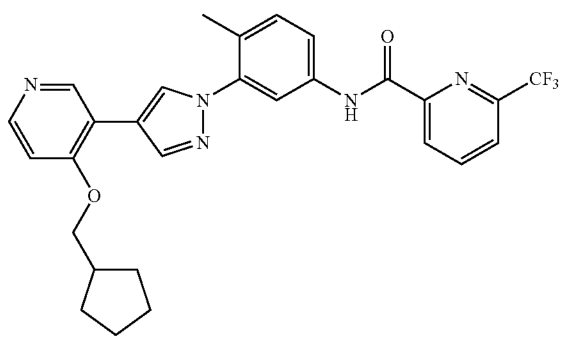 [SMILES: Cc1ccc(NC(=O)c2cccc(C(F)(F)F)n2)cc1-n1cc(-c2cnccc2OCC2CCCC2)cn1] |
| 11 | 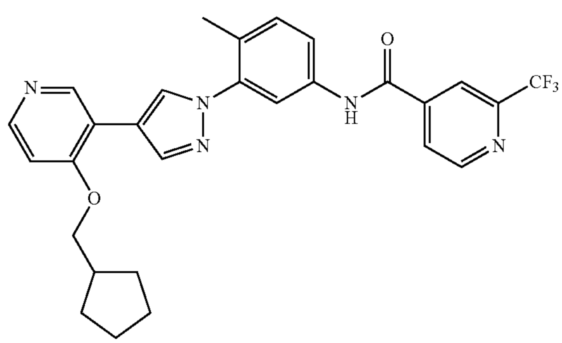 [SMILES: Cc1ccc(NC(=O)c2ccnc(C(F)(F)F)c2)cc1-n1cc(-c2cnccc2OCC2CCCC2)cn1] |

| Compound No. | Compound Structure |
|---|---|
| 12 | 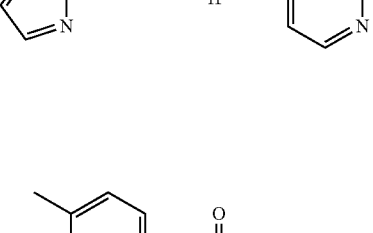 |
| 13 | 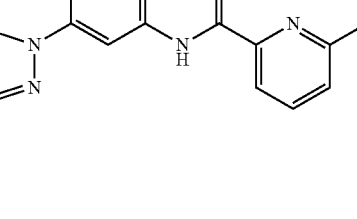 |
| 14 | 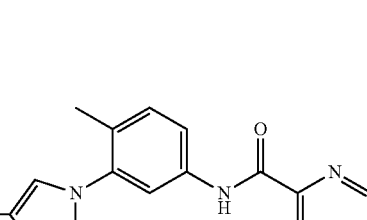 |
| 15 | 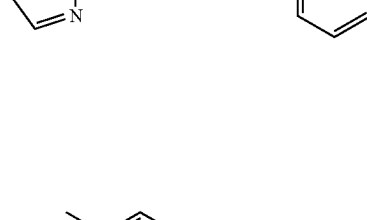 |
| 16 | 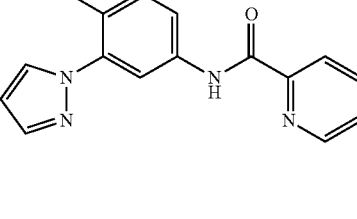 |

-continued

| Compound No. | Compound Structure |
| --- | --- |
| 17 | 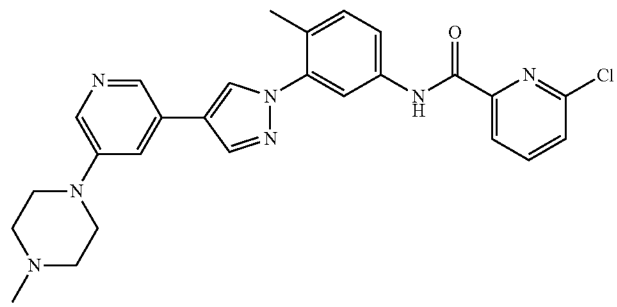 [SMILES: Cc1ccc(NC(=O)c2cccc(Cl)n2)cc1-n1cc(-c2cncc(N3CCN(C)CC3)c2)cn1] |
| 32 | 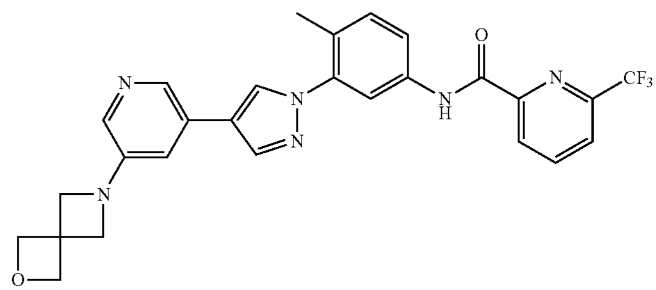 [SMILES: Cc1ccc(NC(=O)c2cccc(C(F)(F)F)n2)cc1-n1cc(-c2cncc(N3CC4(COC4)C3)c2)cn1] |
| 33 | 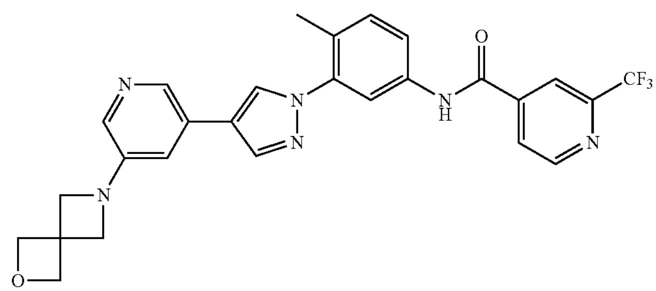 [SMILES: Cc1ccc(NC(=O)c2ccnc(C(F)(F)F)c2)cc1-n1cc(-c2cncc(N3CC4(COC4)C3)c2)cn1] |
| 34 | 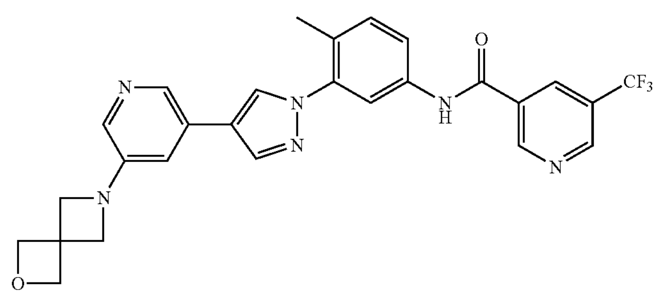 [SMILES: Cc1ccc(NC(=O)c2cncc(C(F)(F)F)c2)cc1-n1cc(-c2cncc(N3CC4(COC4)C3)c2)cn1] |
| 35 | 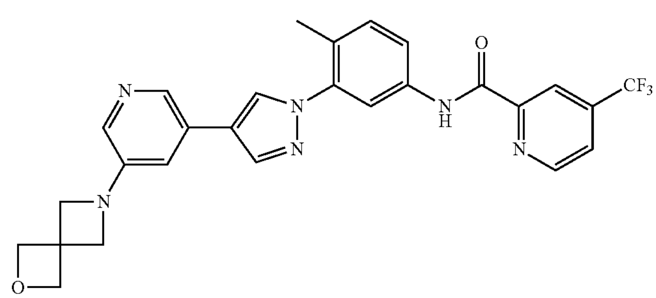 [SMILES: Cc1ccc(NC(=O)c2cc(C(F)(F)F)ccn2)cc1-n1cc(-c2cncc(N3CC4(COC4)C3)c2)cn1] |

| Compound No. | Compound Structure |
|---|---|
| 36 | 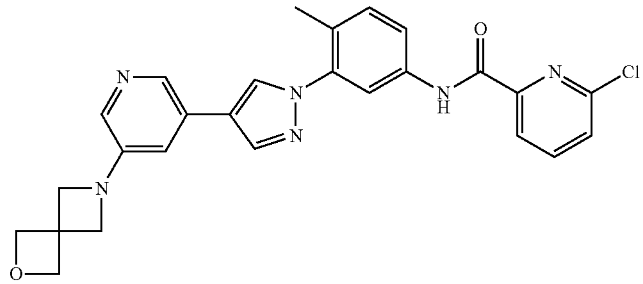 |
| 37 | 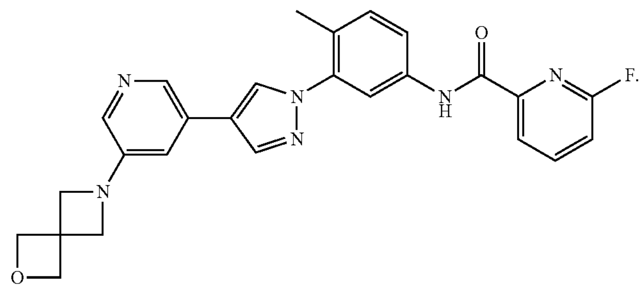 [SMILES: Cc1ccc(NC(=O)c2cccc(Cl)n2)cc1-n1cc(-c2cncc(N3CC4(COC4)C3)c2)cn1] |

10. A pharmaceutical composition, comprising the PDGFR kinase inhibitor according to claim 1, a pharmaceutically acceptable carrier or excipient, and optionally other therapeutic agent.

11. A method for inhibiting the activity of PDGFRα and/or PDGFRβ in a subject in need thereof, comprising a step of administering an effective amount of the PDGFR kinase according to claim 1 to the subject.

12. A method for treating, preventing or ameliorating of a disease, disorder or condition which is modulated or affected by, or involved in the activity of PDGFRα and/or PDGFRβ in a subject in need thereof, comprising a step of administering an effective amount of the PDGFR kinase according to claim 1 to the subject.

13. The method according to claim 12, wherein the disease, disorder, or condition is a proliferative disease selected from the group consisting of pulmonary hypertension, solid tumors, sarcoma, gastrointestinal stromal tumor, colorectal cancer, acute myeloblastic leukemia, chronic myelogenous leukemia, thyroid carcinoma, systemic mastocytosis, eosinophilia syndrome, chronic eosinophilic leukemia, fibrosis, lupus erythematosus, graft versus host disease, neurofibromatosis, pulmonary hypertension, Alzheimer's disease, seminoma, dysgerminoma, mast cell tumors, lung cancer, bronchial carcinoma, testicular intraepithelial neoplasia, melanoma, breast cancer, neuroblastoma, papillary/follicular thyroid carcinoma, malignant lymphoma, non-Hodgkin's lymphoma, multiple endocrine neoplasia type 2, pheochromocytoma, thyroid carcinoma, parathyroid hyperplasia/adenoma, colon cancer, colorectal adenoma, ovarian cancer, prostate cancer, glioblastoma, brain tumor, malignant glioma, pancreatic cancer, malignant pleural mesothelioma, hemangioblastoma, hemangioma, kidney cancer, liver cancer, adrenal carcinoma, bladder cancer, gastric cancer, rectal cancer, vaginal cancer, cervical cancer, endometrial cancer, multiple myeloma, neck and head tumors, neoplasia, or a combination thereof.

14. The method according to claim 12, wherein the disease, disorder, or condition is an autoimmune disease selected from the group consisting of arthritis, rheumatic arthritis, osteoarthritis, lupus, rheumatoid arthritis, inflammatory bowel disease, psoriatic arthritis, Still's disease, juvenile arthritis, diabetes, myasthenia gravis, Hashimoto's thyroiditis, Ord's thyroiditis, Graves' disease, Sjögren's syndrome, multiple sclerosis, Guillain-Barré syndrome, acute disseminated encephalomyelitis, Addison's disease, opsoclonus-myoclonus syndrome, ankylosing spondylitis, antiphospholipid antibody syndrome, aplastic anemia, autoimmune hepatitis, coeliac disease, Goodpasture's syndrome, idiopathic thrombocytopeniaurpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, vulvodynia, or a combination thereof.

15. The method according to claim 12, wherein the disease, disorder, or condition is pulmonary hypertension, chronic eosinophilic leukemia, or a combination thereof.

* * * * *